(12) United States Patent  
Gundlapalli et al.

(10) Patent No.: US 8,083,802 B2  
(45) Date of Patent: *Dec. 27, 2011

(54) PROSTHETIC BEARING WITH ENCAPSULATED REINFORCEMENT

(75) Inventors: Rama Rao V. Gundlapalli, Leesburg, IN (US); Mark Heldreth, Mentone, IN (US); Todd Smith, Ft. Wayne, IN (US); Albert Burstein, Sarasota, FL (US)

(73) Assignee: Deput Products, Inc., Warsaw, IN (US)

( * ) Notice: Subject to any disclaimer, the term of this patent is extended or adjusted under 35 U.S.C. 154(b) by 168 days.

This patent is subject to a terminal disclaimer.

(21) Appl. No.: 12/050,353

(22) Filed: Mar. 18, 2008

(65) Prior Publication Data  
US 2008/0188943 A1    Aug. 7, 2008

Related U.S. Application Data

(62) Division of application No. 10/155,568, filed on May 24, 2002, now abandoned.

(60) Provisional application No. 60/302,115, filed on Jun. 30, 2001.

(51) Int. Cl.  
A61F 2/38    (2006.01)

(52) U.S. Cl. ............ 623/20.28; 623/20.21; 623/23.39; 623/23.58

(58) Field of Classification Search .............. None  
See application file for complete search history.

(56) References Cited

U.S. PATENT DOCUMENTS

| | | | |
|---|---|---|---|
| 3,886,600 A * | 6/1975 | Kahn et al. ............ | 623/20.24 |
| 4,209,861 A | 7/1980 | Walker et al. | |
| 4,213,209 A | 7/1980 | Insall et al. | |
| 4,257,129 A | 3/1981 | Volz | |
| 4,298,992 A | 11/1981 | Burstein | |
| 4,501,031 A | 2/1985 | McDaniel | |
| 4,822,366 A | 4/1989 | Bolesky | |
| 4,865,607 A * | 9/1989 | Witzel et al. ............ | 623/20.32 |
| 4,874,389 A * | 10/1989 | Downey .............. | 623/17.16 |
| 4,892,547 A | 1/1990 | Brown | |
| 4,959,071 A | 9/1990 | Brown et al. | |
| 4,997,445 A | 3/1991 | Hodorek | |
| 5,007,933 A | 4/1991 | Sidebotham et al. | |
| 5,011,496 A * | 4/1991 | Forte et al. ............ | 623/20.27 |
| 5,139,521 A | 8/1992 | Schelhas | |
| 5,147,405 A | 9/1992 | Van Zile et al. | |

(Continued)

FOREIGN PATENT DOCUMENTS  
DE    4434806 A1    4/1996  
(Continued)

OTHER PUBLICATIONS

Insall, John N., "Surgery of the Knee", (Churchill Livingstone) (1984), p. 680.

(Continued)

*Primary Examiner* — David H Willse  
*Assistant Examiner* — Javier G Blanco

(57) ABSTRACT

A joint prosthesis has a first component for cooperation with a first long bone, a second component for cooperation with a second long bone, and a bearing component positionable between the first component and the second component. The bearing component includes a reinforcing component and a polymeric material completely encapsulating the reinforcing component and molded thereto. The bearing component may be sterilized by a predominately surface sterilizing technology.

18 Claims, 24 Drawing Sheets

U.S. PATENT DOCUMENTS

| | | | |
|---|---|---|---|
| 5,176,684 A | 1/1993 | Ferrante et al. | |
| 5,282,866 A | 2/1994 | Cohen | |
| 5,330,534 A | 7/1994 | Herrington et al. | |
| 5,358,527 A | 10/1994 | Forte et al. | |
| 5,370,699 A | 12/1994 | Hood et al. | |
| 5,405,396 A | 4/1995 | Heldreth et al. | |
| 5,413,604 A | 5/1995 | Hodge | |
| 5,549,686 A | 8/1996 | Johnson et al. | |
| 5,577,368 A | 11/1996 | Hamilton et al. | |
| 5,609,643 A | 3/1997 | Colleran et al. | |
| 5,658,344 A | 8/1997 | Hurlburt | |
| 5,683,470 A | 11/1997 | Johnson et al. | |
| 5,702,458 A | 12/1997 | Burstein et al. | |
| 5,702,460 A | 12/1997 | Carls et al. | |
| 5,755,808 A | 5/1998 | DeCarlo et al. | |
| 5,776,200 A | 7/1998 | Johnson et al. | |
| 5,824,103 A | 10/1998 | Williams | |
| 5,830,396 A | 11/1998 | Higgins | |
| 5,871,546 A | 2/1999 | Colleran et al. | |
| 5,944,756 A | 8/1999 | Fischetti et al. | |
| 5,944,759 A * | 8/1999 | Link | 623/18.11 |
| 5,989,472 A | 11/1999 | Ashby et al. | |
| 5,997,577 A | 12/1999 | Herrington et al. | |
| 6,004,351 A | 12/1999 | Tomita et al. | |
| 6,004,352 A | 12/1999 | Bunl | |
| 6,010,534 A | 1/2000 | O'Neil et al. | |
| 6,017,975 A | 1/2000 | Saum et al. | |
| 6,039,764 A | 3/2000 | Pottenger et al. | |
| 6,099,570 A | 8/2000 | Livet et al. | |
| 6,123,728 A | 9/2000 | Brosnahan | |
| 6,123,729 A | 9/2000 | Insall et al. | |
| 6,125,255 A | 9/2000 | Litman et al. | |
| 6,126,692 A | 10/2000 | Robie et al. | |
| 6,165,220 A * | 12/2000 | McKellop et al. | 128/898 |
| 6,165,223 A | 12/2000 | Metzger et al. | |
| 6,228,900 B1 | 5/2001 | Shen et al. | |
| 6,242,507 B1 | 6/2001 | Saum et al. | |
| 6,306,172 B1 | 10/2001 | O'Neil et al. | |
| 6,315,798 B1 * | 11/2001 | Ashby et al. | 623/20.17 |
| 6,413,279 B1 | 7/2002 | Metzger et al. | |
| 6,475,241 B2 | 11/2002 | Pappas | |
| 6,620,198 B2 | 9/2003 | Burstein et al. | |
| 6,660,039 B1 | 12/2003 | Evans et al. | |
| 2003/0009231 A1 | 1/2003 | Gundlapalli et al. | |

FOREIGN PATENT DOCUMENTS

| | | |
|---|---|---|
| EP | 0724868 A1 | 7/1996 |
| EP | 0705580 | 12/1999 |
| EP | 0963824 A2 | 12/1999 |
| EP | 1133959 A1 | 9/2001 |
| EP | 1270187 A3 | 2/2004 |
| FR | 2760352 | 10/1997 |
| GB | 1507309 | 10/1975 |
| JP | 51-127955 | 10/1976 |
| WO | 95/21212 A1 | 8/1995 |

OTHER PUBLICATIONS

Dorr, et al., "Bone Graft for Tibial Defects in Total Knee Arthroplasty," Clinical Orthopaedics and Related Research, No. 205 (1986): 153-165.

Donaldson, et al., "Total Condylar III Knee Prosthesis: Long-Term Follow-Up Study," Clinical Orthopaedics and Related Research, No. 226 (1988): 21-28.

Merkow, et al., "Patellar Dislocation Following Total Knee Replacement", The Journal of Bone and Joint Surgery, vol. 67-A, No. 9 (1985) 1321-1327.

Scott, Richard D., Revision Total Knee Arthroplasty, Clinical Orthopaedics and Related Research, No. 226 (1988): 65-77.

Scott, et al., Press-Fit Condylar Total Kenee Replacement, The Orthopedic Clinics of North America, Surgical Reconstruction of the Arthritic Knee I (1989): 89-95.

Stern, et al., "Total Knee Arthroplasty With Posterior Cruciate Ligament Substitution Designs", Surgery of the Knee, Second Edition, Edited by Insall, et al (1993), Ch. 29: 829-867.

Westrich, et al., Disengagement of a Locking Screw From a Modular Stem in Reivison Total Knee Arthroplasty: A Report of Three Cases, The Journal of Bone and Joint Surgery, vol. 79A, No. 2 (1997) 254-258.

AMK Total Knee System, The Modular Knee System That Meets Surgeons' Needs From Primary to Revision Surgery, Depuy, A Johnson & Johnson Company, 5M0200 (0601-42-050) (2000).

Japanese Search Report for Corresponding Patent Application No. 2002-192592, Dated May 13, 2008, 3 Pages.

* cited by examiner

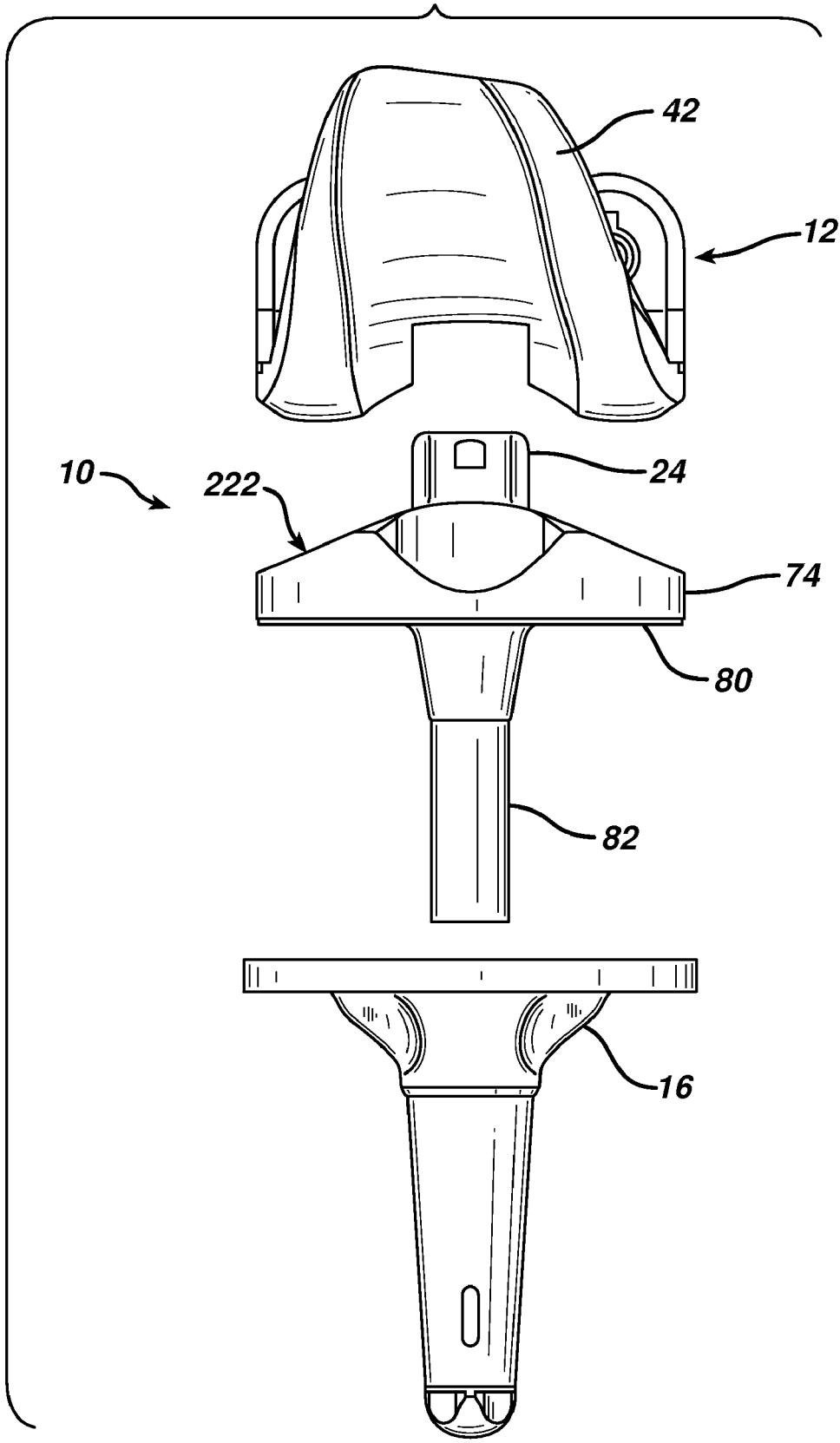

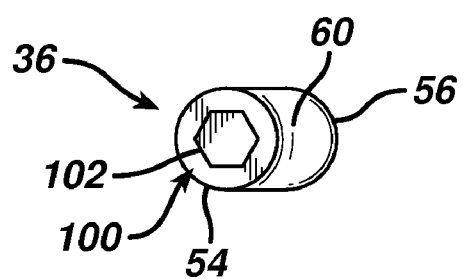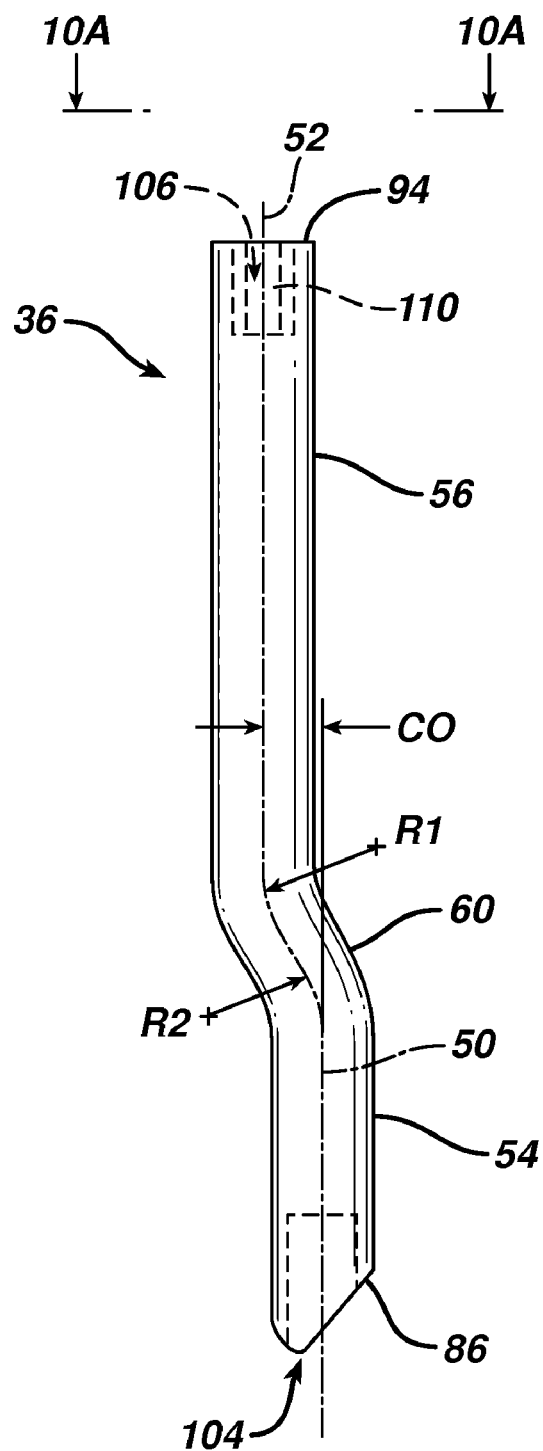

PROSTHETIC BEARING WITH ENCAPSULATED REINFORCEMENT

CROSS REFERENCE TO U.S. PROVISIONAL PATENT APPLICATION

This application is a divisional of U.S. patent application Ser. No. 10/155,568, filed May 24, 2002, now abandoned, which is based upon U.S. Provisional Patent Application Ser. No. 60/302,115 filed Jun. 30, 2001, entitled SURFACE STERILIZABLE JOINT REPLACEMENT PROSTHESIS COMPONENT WITH INSERT, now expired.

CROSS-REFERENCE TO RELATED APPLICATIONS

Cross reference is made to the following patents: U.S. Pat. No. 6,821,470, entitled "JOINT PROSTHESIS MOLDING METHOD AND DIE FOR PREFORMING THE SAME" and U.S. Pat. No. 6,962,607 entitled "JOINT REPLACEMENT PROSTHESIS COMPONENT WITH NON LINEAR INSERT", both filed on May 24, 2002, which are incorporated herein by reference herein in their entireties.

TECHNICAL FIELD OF THE INVENTION

The present invention relates generally to the field of orthopaedics, and more particularly, to an implant for use in joint arthroplasty.

BACKGROUND OF THE INVENTION

The invention relates to joint prostheses. More particularly, the invention is directed to tibial components of knee joint prostheses that can be configured to be either rotatable or non-rotatable.

Joint replacement surgery is quite common and it enables many individuals to function normally when otherwise it would not be possible to do so. Artificial joints usually comprise metallic, ceramic and/or plastic components that are fixed to existing bone.

Knee arthroplasty is a well known surgical procedure by which a diseased and/or damaged natural knee joint is replaced with a prosthetic knee joint. A typical knee prostheses include a femoral component, a patella component, a tibial tray or plateau, and a tibial bearing insert. The femoral component generally includes a pair of laterally spaced apart condylar portions, the distal surfaces of which articulate with complementary condylar elements formed in a tibial bearing insert.

The tibial plateau is mounted within the tibia of a patient. Typically, the tibial bearing insert, which is usually made of ultra high molecular weight polyethylene (UHMWPE), is mounted upon the superior surface of the tibial plateau. The geometry and structure of the tibial bearing insert varies depending upon the needs and joint condition of a patient. Some tibial bearing inserts are designed to be used with joint prostheses that are implanted during procedures that retain one or both of the cruciate ligaments. Others are implanted after removal of one or both of the cruciate ligaments, and are thus structured to compensate for the loss of these ligaments. Yet other tibial bearing inserts are used with prostheses that provide enhanced stabilization to the knee joint.

Recent total knee prostheses have been designed which allow for increased freedom of rotation between the femur and the tibia. To allow for this rotational motion, tibial bearing inserts have been designed which allow for rotation of the insert on the tibial tray or plateau. Typically the tibia bearing inserts have a central stem which rotationally engages centrally in the tibial stem of the tibial tray implant, thereby providing for the rotational motion. Typically, there are no rotational constraints between the tibial tray implant and the tibial bearing insert. Frequently, during total knee arthroplasty, the posterior cruciate ligaments are sacrificed and a substitute for the posterior cruciate ligaments is required. Orthopaedic implants for total knee arthroplasty have been developed which provide for the substitution of the posterior cruciate ligament. Examples of such implants include the PFC Sigma RP as described in U.S. Pat. No. 4,298,992 incorporated herein by reference, and the LCS Complete total knee prosthesis, both of which are sold by DePuy Orthopaedics, Inc., Warsaw, Ind.

These total knee prostheses are designed with tibial components and femoral components which have in conjunction with their articulating surface, a spine and cam mechanism, which is used as a posterior cruciate substituting feature when the posterior cruciate of the knee is sacrificed.

Such total knee replacement prostheses, which include a spine and cam mechanism, typically contain tibial bearing components manufactured from suitable plastic, usually UHMWPE. One such construction use for a class of total knee replacement prosthesis, which are known as constrained prosthesis, often incorporate metal reinforcement rods in the construction of the plastic bearing component. The bearing insert is constructed so that the metal rod lies within the bearing, and thus provides additional support for the central spine element of the bearing. Such components are typically manufactured by machining or molding the bearing component, drilling a central hole, and press fitting the reinforcing metal rod. An example of such a component is described in U.S. Pat. No. 5,007,933 to Sidebotham et al. hereby incorporated in its entirety by reference.

In order to allow for desired kinematics of the knee during a full range of motion, the spine and cam mechanism on the tibial bearing insert may be placed in a suitable position, preferably anterior to the center line of the insert in the anterior/posterior direction. Designs of tibial inserts are available to help reconstruct knees where the stabilizing soft tissue compromises have been made or occurred due to various reasons. In such cases, the tibial bearing inserts are required to experience greater loads in the anterior/posterior and the medial/lateral directions. The constrained inserts may be reinforced with a metal rod, as mentioned earlier, to help distribute the loads experienced by the spine of the polyethylene tibial bearing.

Total knee joint prostheses have been designed with the spine and cam mechanism on the tibial bearing insert placed in a position that the central axis of the distal stem portion of the insert that engages the tibial tray, and the axis of the superior spine portion that engages the cam of the femoral component, are not necessarily collinear.

Unfortunately, this design does not allow for a straight rod, commonly employed for reinforcement of tibial bearing inserts, to be used.

It should be appreciated that a first rod could be inserted inside the spine, and a second rod could be inserted in the stem of the tibial tray portion of the bearing insert. However, the load on the first rod would be transferred through the polymer portion of the insert to the second rod. The polymer strength would then limit the load carrying capacity of this configuration. Such a configuration may not provide the required strength to sufficiently support and reinforce the spine.

The present invention is directed to providing a tibial bearing insert with sufficient strength at the spine to withstand the loads of the knee prosthesis in the anterior/posterior and medial/lateral direction, while preserving bearing wear resistance when the central axis of the distal stem of the insert and the axis of the superior spine are not necessarily co-linear.

SUMMARY OF THE INVENTION

The present invention is directed to an improved joint prosthesis for total knee replacement which includes a spine and cam mechanism, the cam mechanism being on the femoral component and the spine being on the bearing component. The mechanism is capable of withstanding the greater loads experienced in the anterior/posterior and medial/lateral direction caused by the substitution of the cam and spine for the posterior cruciate ligament which may be sacrificed during total knee arthroplasty while preserving bearing wear resistance.

The spine on the tibial bearing insert, according to the present invention, is placed anterior to the centerline of the insert in the anterior/posterior direction. Therefore, the distal stem portion of the insert which engages the tibial tray and the superior spine portion which engages the cam of the femoral component are not in the same plane. The tibial bearing insert of the present invention thus includes a rod placed internal to the tibial bearing insert which includes an offset feature.

The knee prosthesis of the present invention thus includes a first polymeric component and a reinforcing component including a first portion on a first center line and a second portion on a second center line such that the first portion may engage the tibial tray and the second portion may be cooperating with the cam mechanism in the femoral component of the knee prosthesis.

According to one embodiment of the present invention, there is provided a first component for cooperation with a first long bone a a second component for cooperation with a second long bone, and a bearing component positionable between said first component and said second component and cooperable therewith. The bearing component includes a reinforcing component having a first end and a second end thereof and a polymeric material completely encapsulating the reinforcing component and molded thereto. The bearing component may be sterilized by a predominately surface sterilizing technology.

According to another embodiment of the present invention, there is provided a method of manufacturing a polymeric bearing component for use in joint arthroplasty and for cooperation with a first joint component and a second joint component. The method comprises the steps of providing a reinforcing support, providing a molding die adapted for manufacturing the bearing component and providing a positioning member for cooperation with the reinforcing support and molding die. The reinforcing support is positioned in a desired position within the molding die; this position is maintained with the positioning member in intimate contact with the reinforcing support. A moldable polymeric material is added into the molding die and the reinforcing support is substantially surrounded with the moldable material. The mold is heated and pressurized. The positioning member is removed from the reinforcing support and the polymeric material is allowed to replace the space occupied by the positioning member. The bearing component is removed from the molding die and sterilized by a predominantly surface sterilization technique.

If a total knee prosthesis requires removal from the patient and replacement with a new prosthesis, such replacement prosthesis typically engages further into the medullary canals of the femur and tibia. Such prostheses are called revision prosthesis. During the prosthesis replacement, cruciate ligaments are much more often sacrificed than in an initial or primary total knee arthroplasty. Currently, no revision tibial bearing inserts with rotational features include a spine which centerline is not aligned with the center of the distal stem portion of the insert which rotationally engages the tibial tray.

Attempts have been made to reinforce polyethylene bearings. One such attempt is that as shown in U.S. Pat. No. 5,989,472 Ashby et al, incorporated herein by reference. The polyethylene bearing in Ashby includes a reinforcement feature for bone attachment. The reinforcement feature is to assist in eliminating motion between the polyethylene and the metal backing.

Another attempt at reinforcing a polyethylene bearing is described in U.S. Pat. No. 4,997,445 to Hodoreck incorporated herein by reference. This patent describes a metal backed prosthesis implant with enhanced bonding of polyethylene to the metal base.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 9 is a fully exploded elevation view from the anterior showing the plastic bearing component removed from the tibial;

FIG. 10 is a plan view of a reinforcing rod for use with the bearing component for an embodiment of the prosthesis of the present invention;

FIG. 10A is a view of the reinforcing rod of FIG. 10 along the line 10A-10A in the direction of the arrows;

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
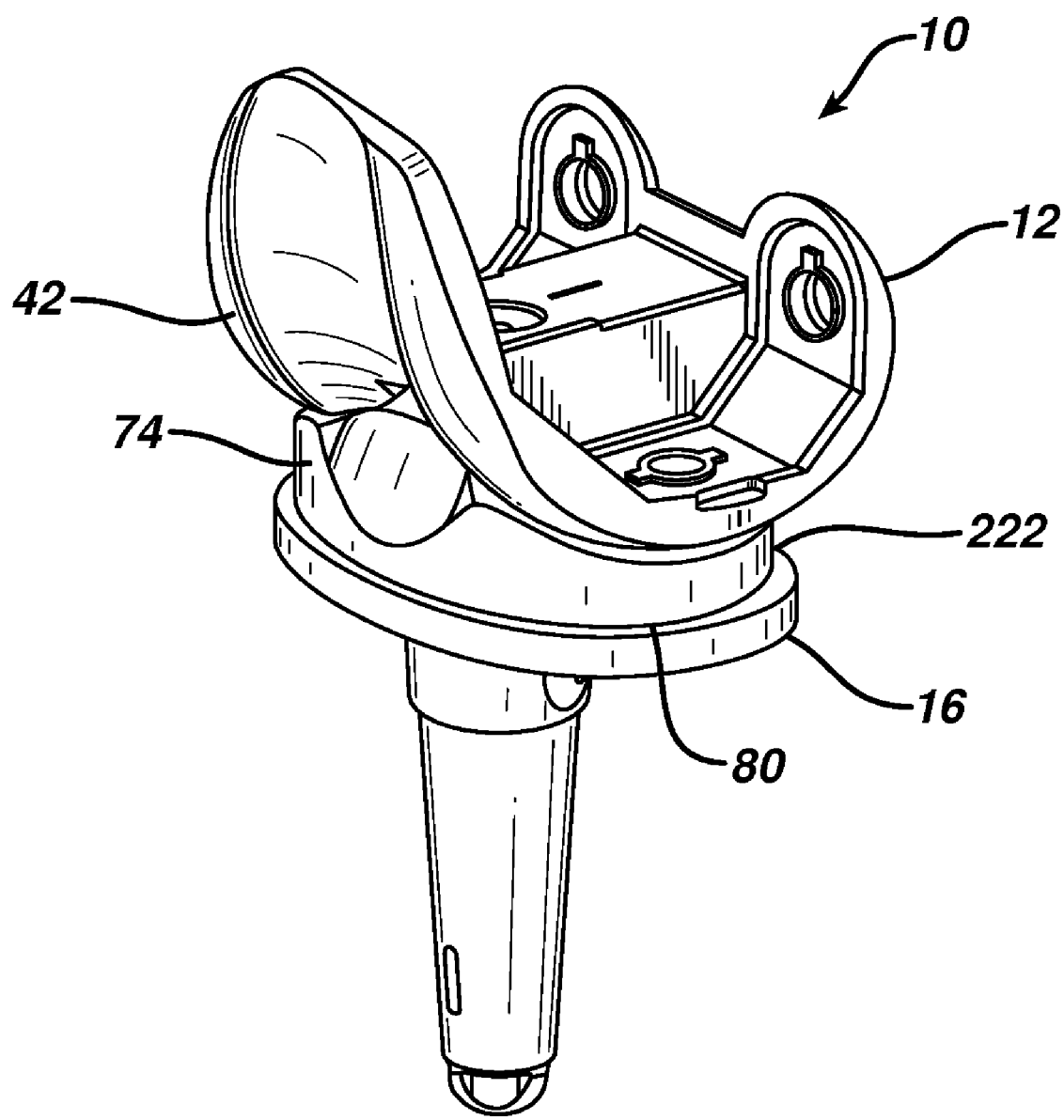
FIG. 1 is a perspective view of the knee system including the bearing component of the present invention showing the femoral component and the tibial tray component with the tibial bearing showing the knee system in extension.
Figure 2:
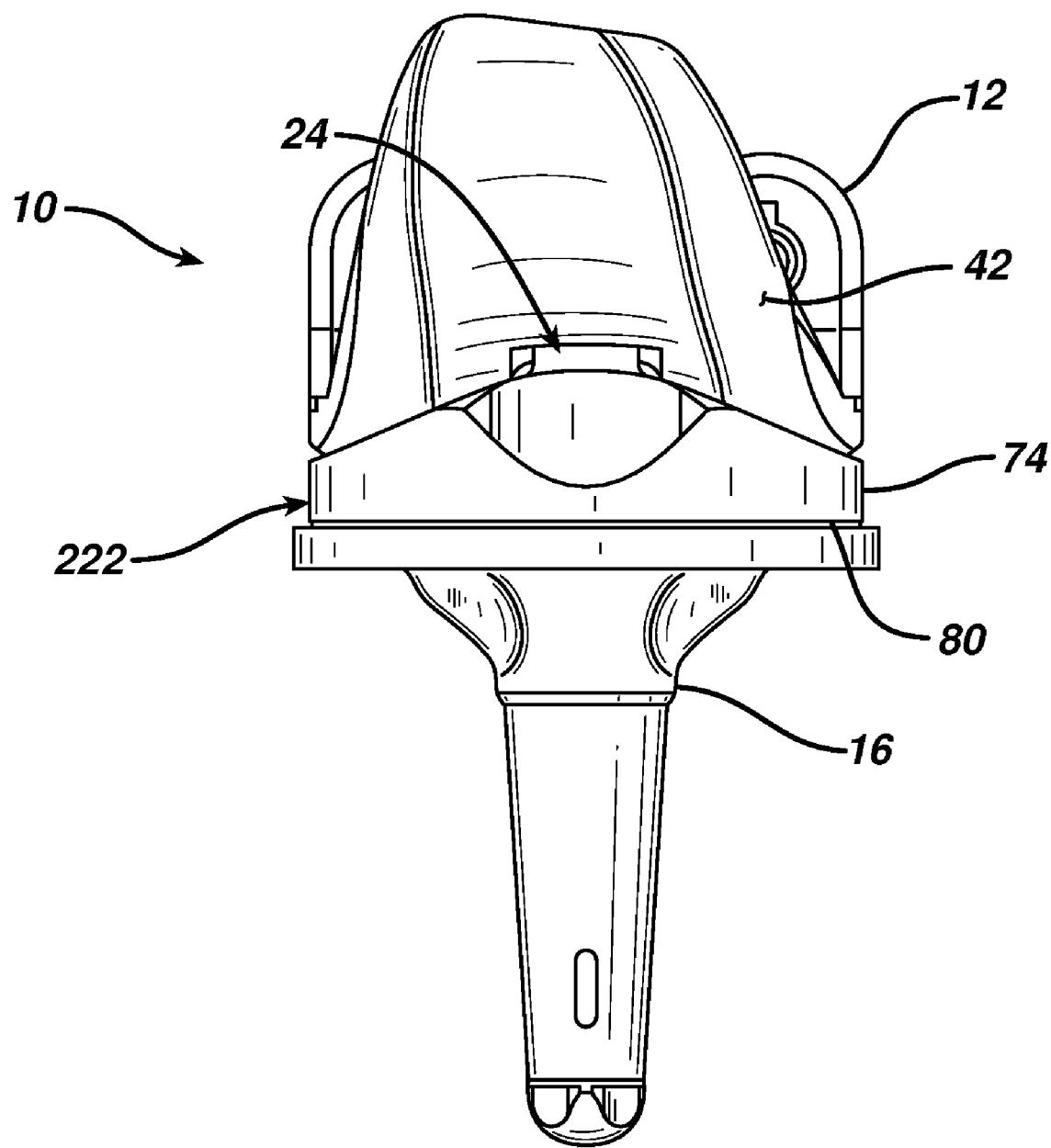
FIG. 2 is an elevation view from the anterior of FIG. 1.
Figure 3:
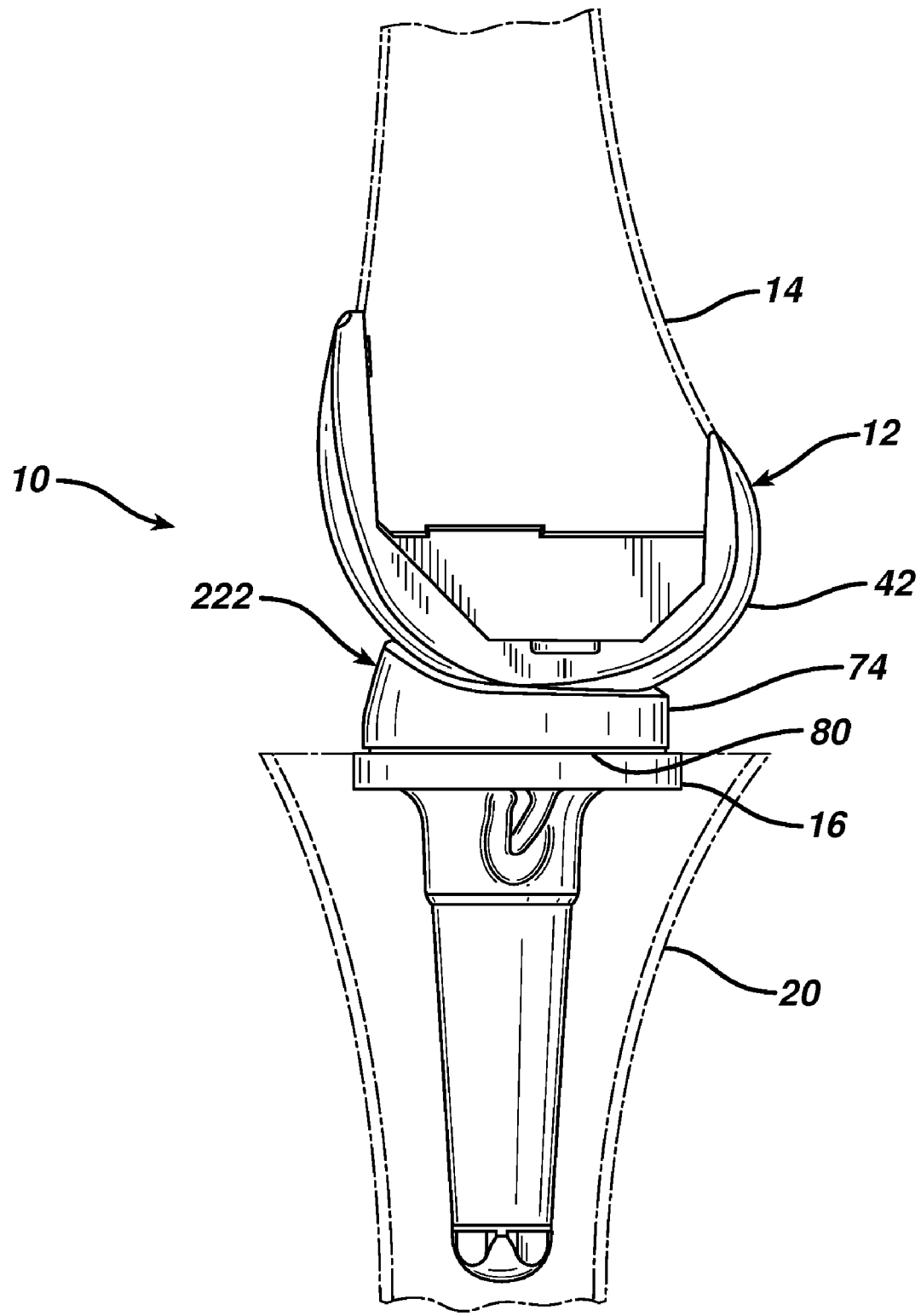
FIG. 3 is a side view of the assembly shown in FIGS. 1 and 2.
Figure 4:
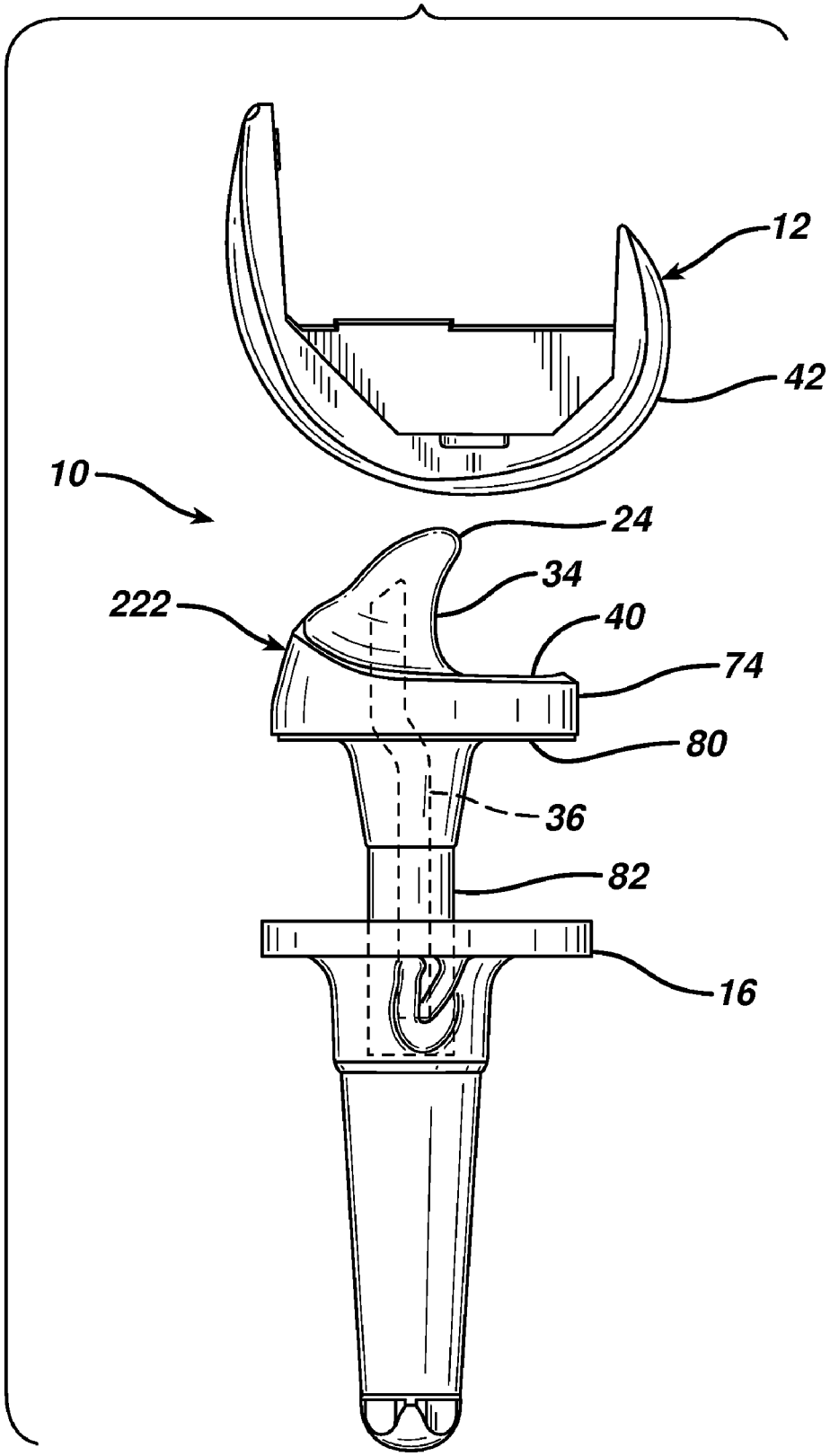
FIG. 4 is an exploded side view showing the plastic bearing component partially removed from the tibial tray or plateau.
Figure 5:
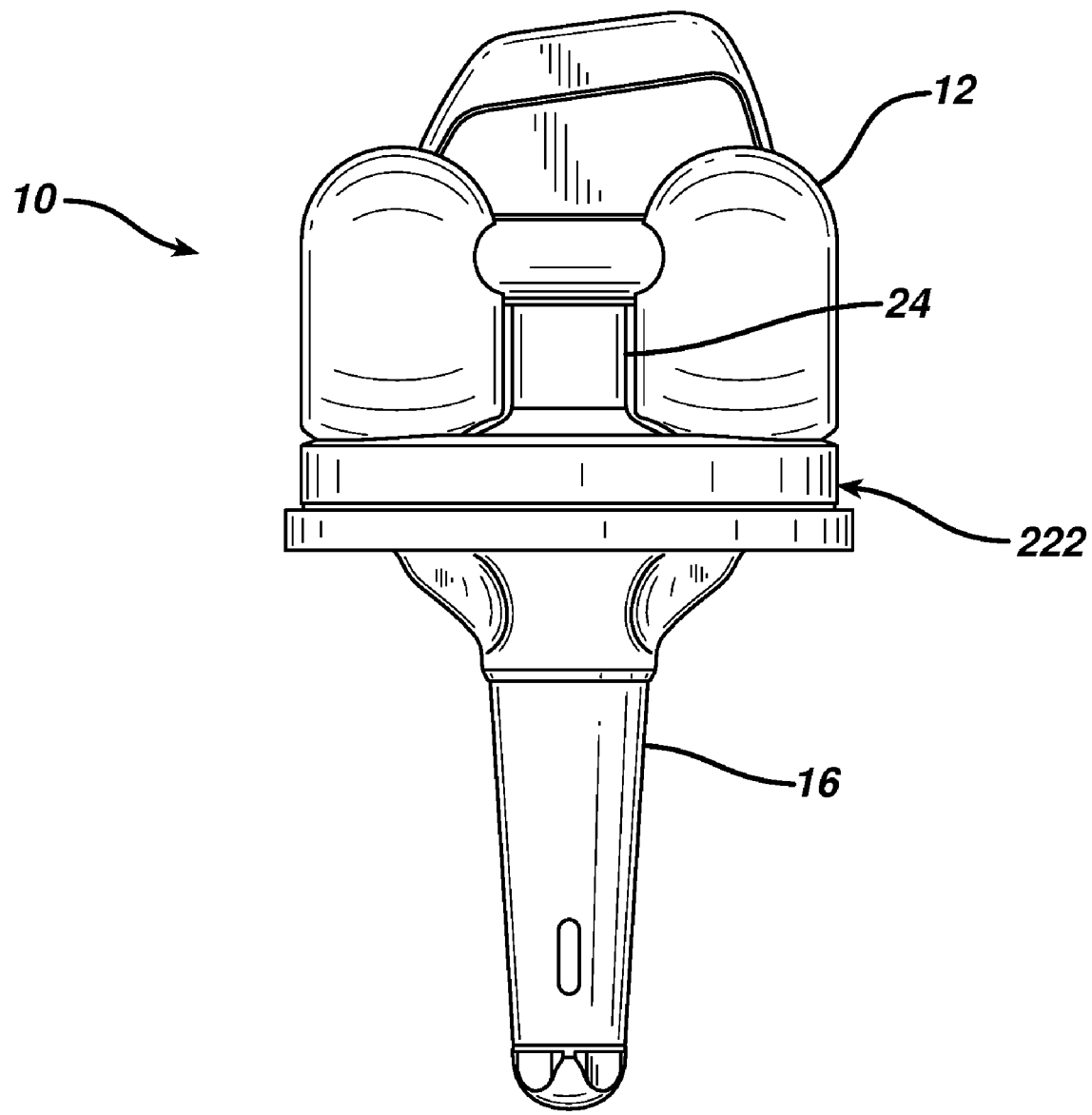
FIG. 5 is an elevation view from the posterior of FIG. 1.
Figure 6:
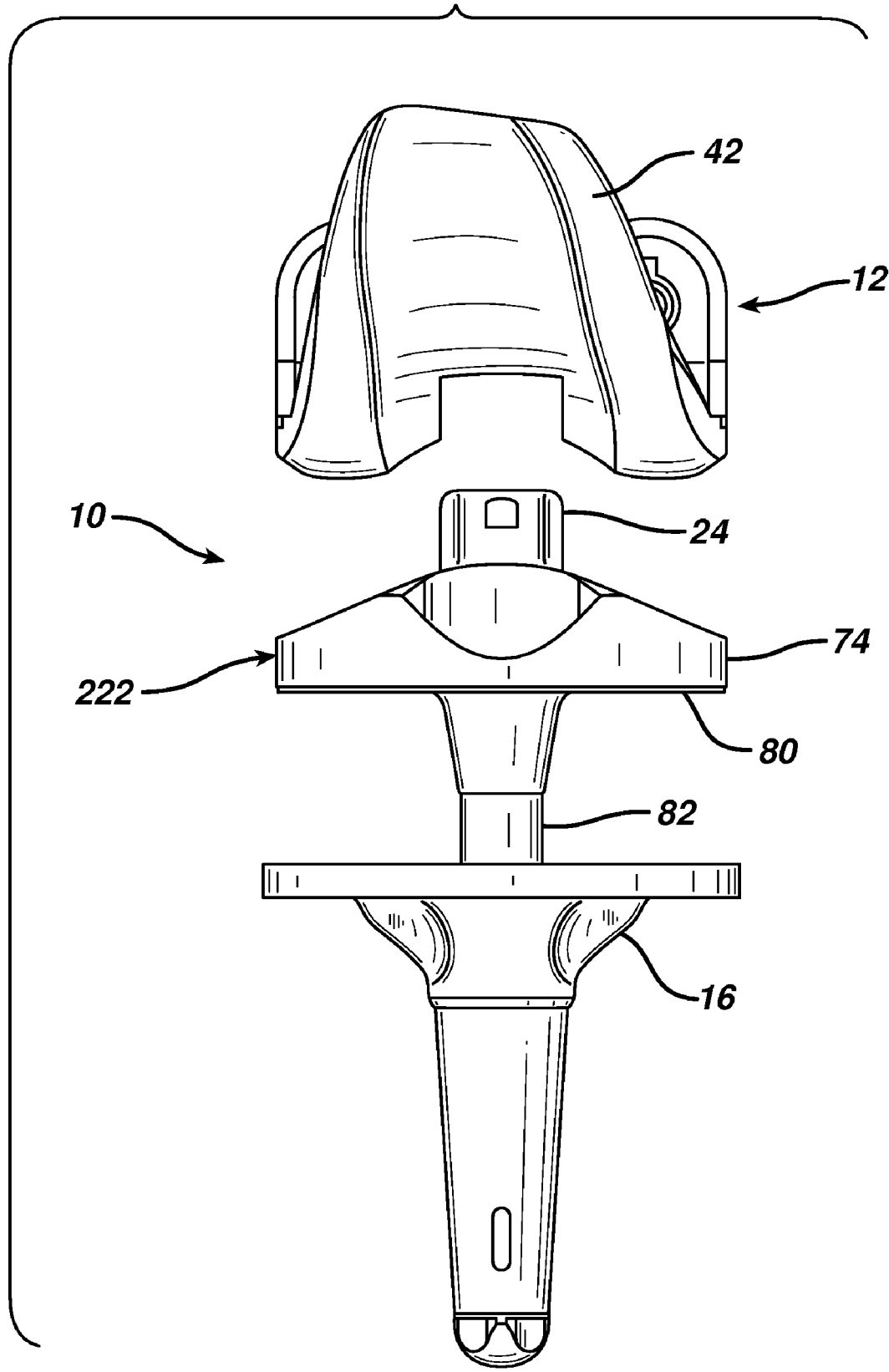
FIG. 6 is an exploded elevation view from the anterior showing the plastic bearing component partially removed from the tibial tray or plateau.
Figure 7:
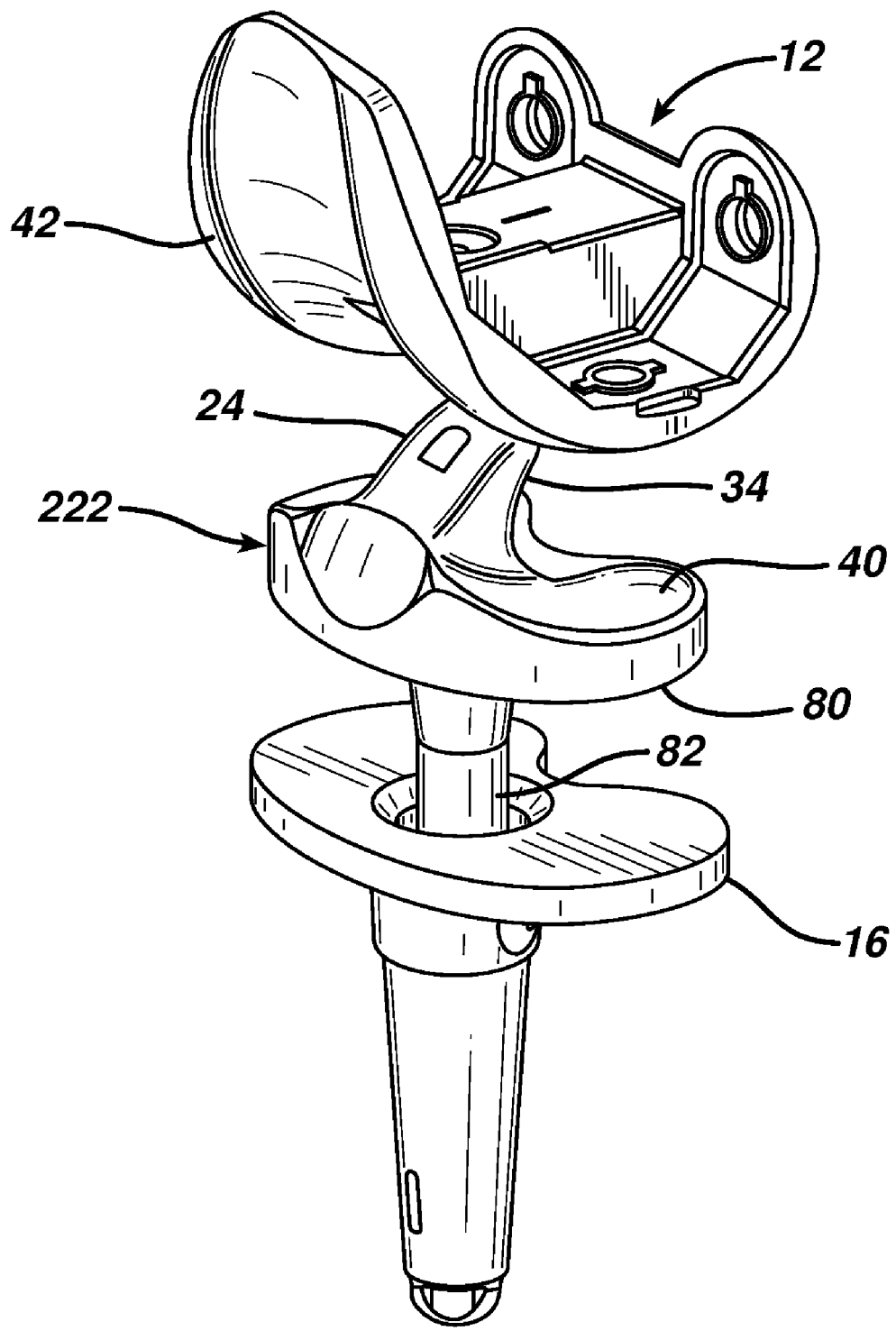
FIG. 7 is an exploded perspective view showing the plastic bearing component partially removed from the tibial tray or plateau.
Figure 8:
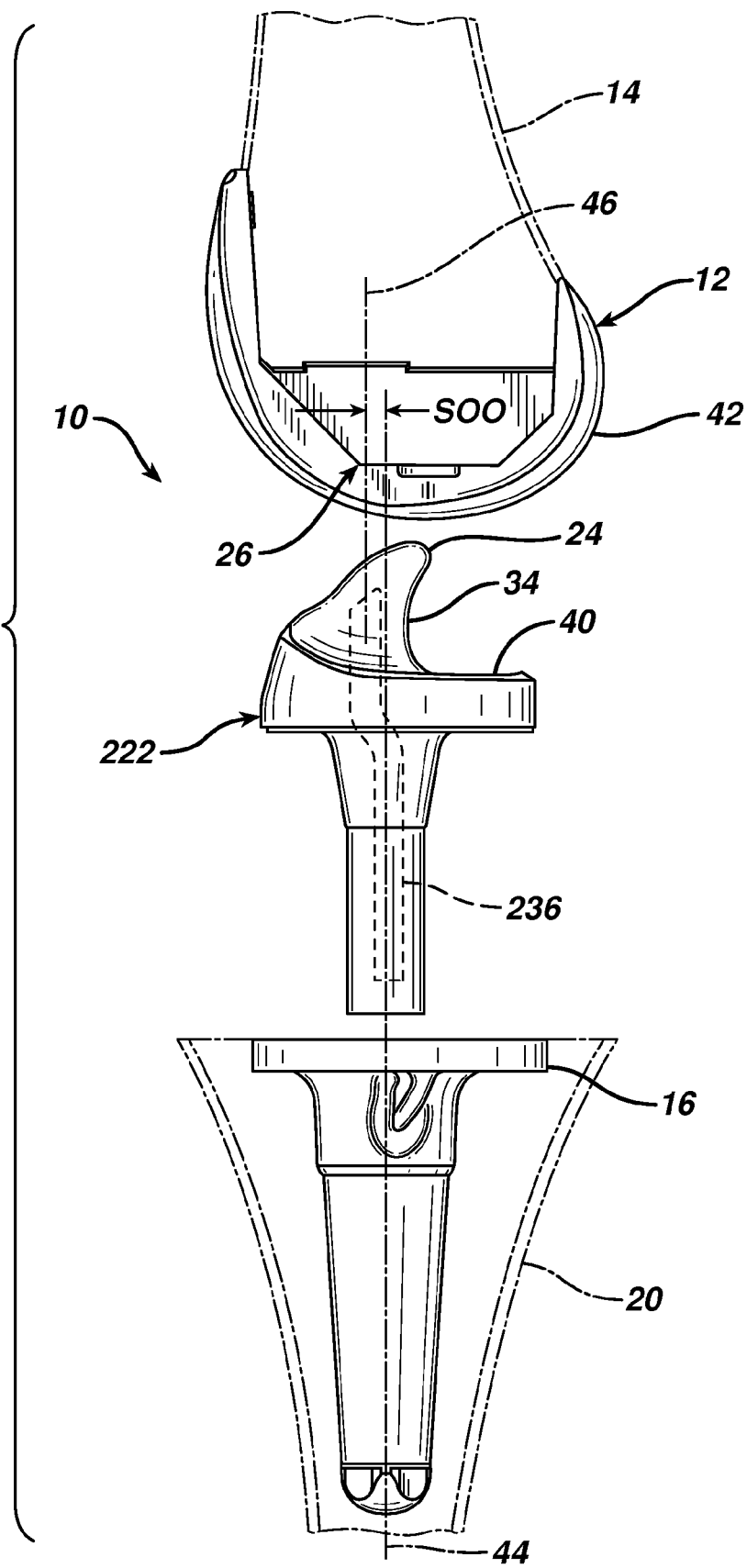
FIG. 8 is a fully exploded side view showing the plastic bearing component removed from the tibial.

According to the present invention and referring now to FIG. 8, a joint prosthesis in the form of knee prosthesis 10 as shown. The knee prosthesis 10 includes a femoral component or first joint component 12 for attachment to femur or first long bone 14. The prosthesis 10 further includes a tibial tray or second joint component 16 for attachment to tibia or second long bone 20. The femoral component 12 and the tibial component 16 are shown in greater detail in FIGS. 1-9 and 21-24. The femoral component 12 and the tibial component 16 are made of any suitable durable material which are biologically compatible with the human anatomy. The femoral component 12 and the tibial component 16 may, for example, be made of a metal alloy, for example, cobalt-chromium-molybdenu-m, a titanium and its alloys, or be made of stainless steel.

The knee prosthesis 10 further includes a bearing component 222. The bearing component 222 is positionable between the femoral component 12 and the tibial tray 16. The bearing component 222 cooperates with the femoral component 12 and the tibial tray 16 to provide for the kinematics of the knee prosthesis.

The prosthesis, as shown in FIGS. 1-9 and 21-24, are commonly referred to as a mobile bearing prosthesis or a mobile bearing knee. Such mobile bearing knees have been provided by DePuy Orthopaedics, Inc. under the trade name LCS since about 1977. Mobile bearing knees of this type are different than fixed bearing knees in that the tibial component 20 and the bearing component 222 may be physically separated from each other. The bearing component is also allowed to have rotational freedom about the tibial tray component. The use of mobile bearing knees may require that the patient have satisfactory cruciate collateral ligaments and tendons necessary to maintain the proper relationship of the femoral component to the bearing component. In those cases where the cruciate ligaments are either severely damaged or have been sacrificed or removed during a knee surgery, provisions must be made within the prosthesis to constrain the femoral component with respect to the tibial tray.

Figure 21:
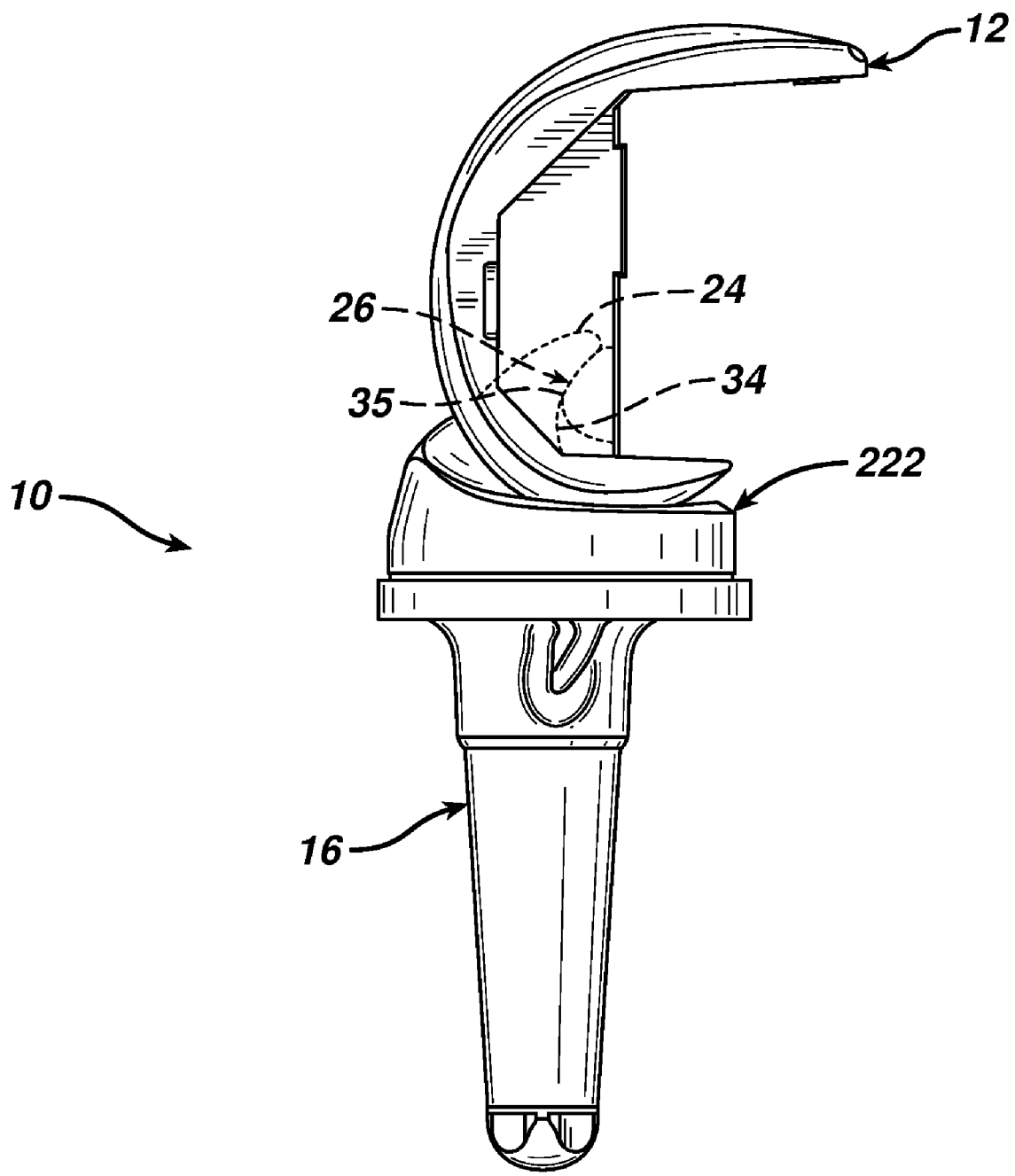
FIG. 21 is a side view of the assembly shown in FIGS. 1 and 2 showing the assembly in flexion.
Figure 22:
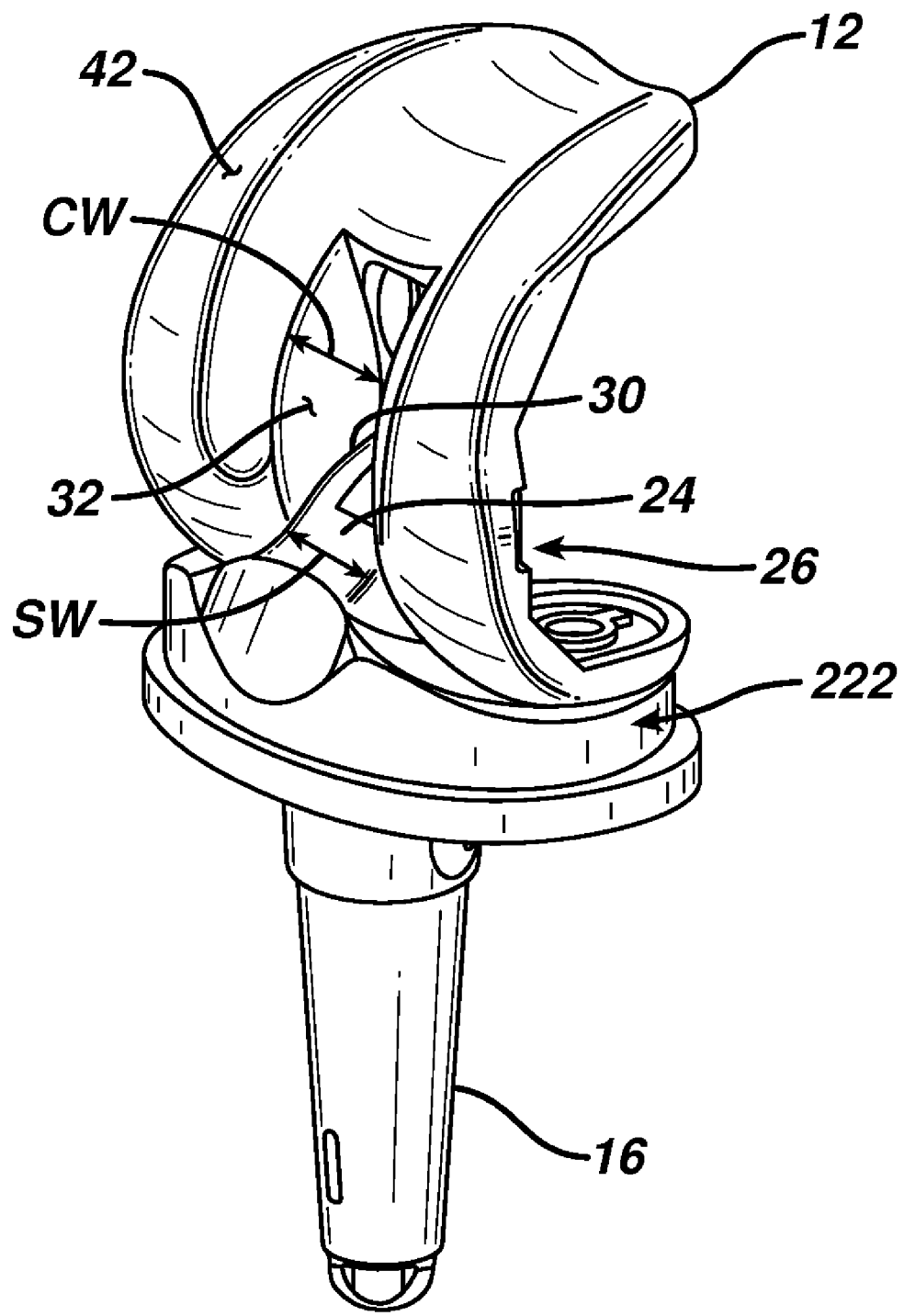
FIG. 22 is a perspective view of the knee system of FIG. 1 including the bearing component of the present invention showing the femoral component and the tibial component with the tibial bearing showing the knee system in flexion.
Figure 23:
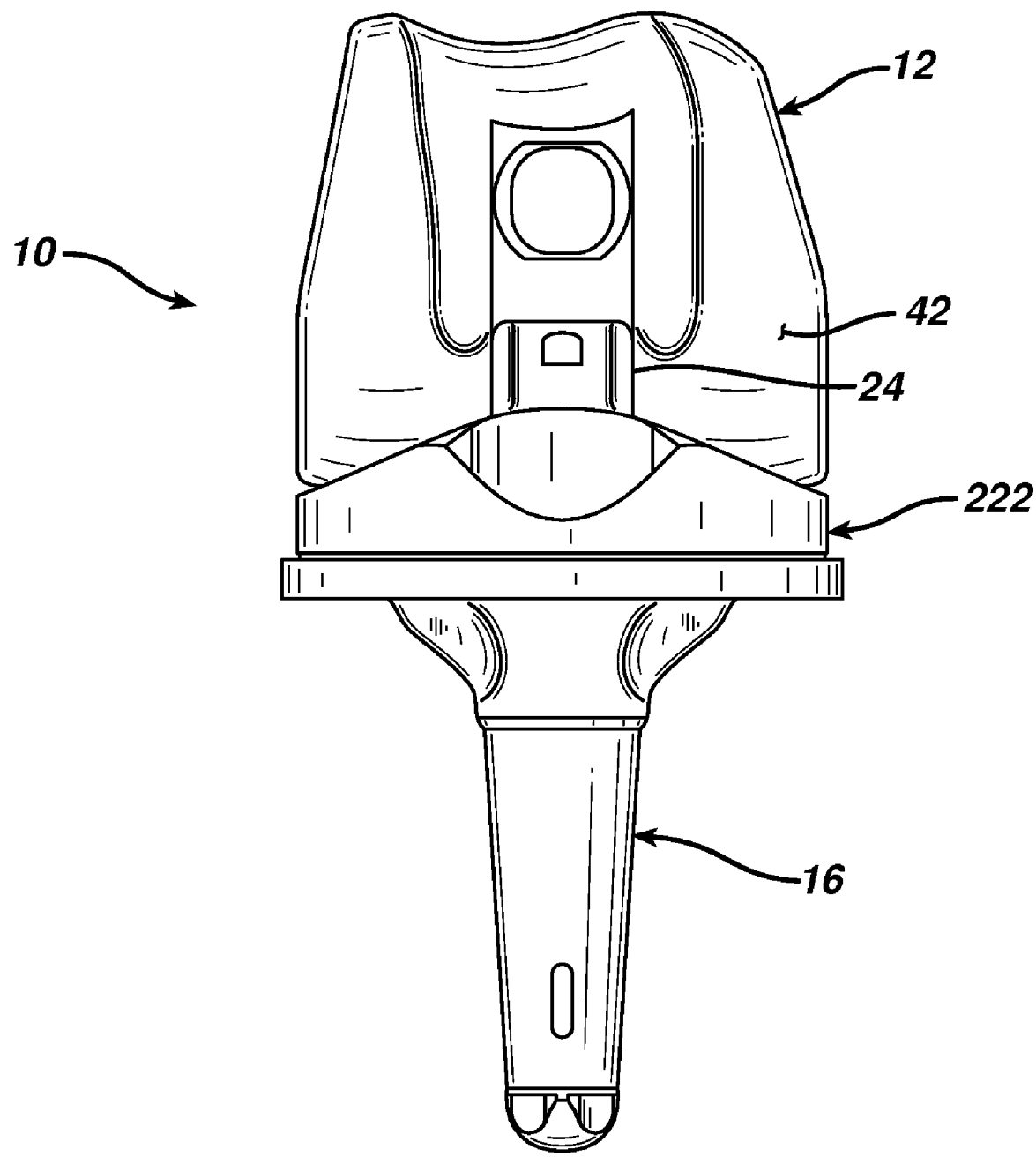
FIG. 23 is an elevation view from the anterior side of the assembly shown in FIGS. 1 and 2 showing the assembly in flexion.
Figure 24:
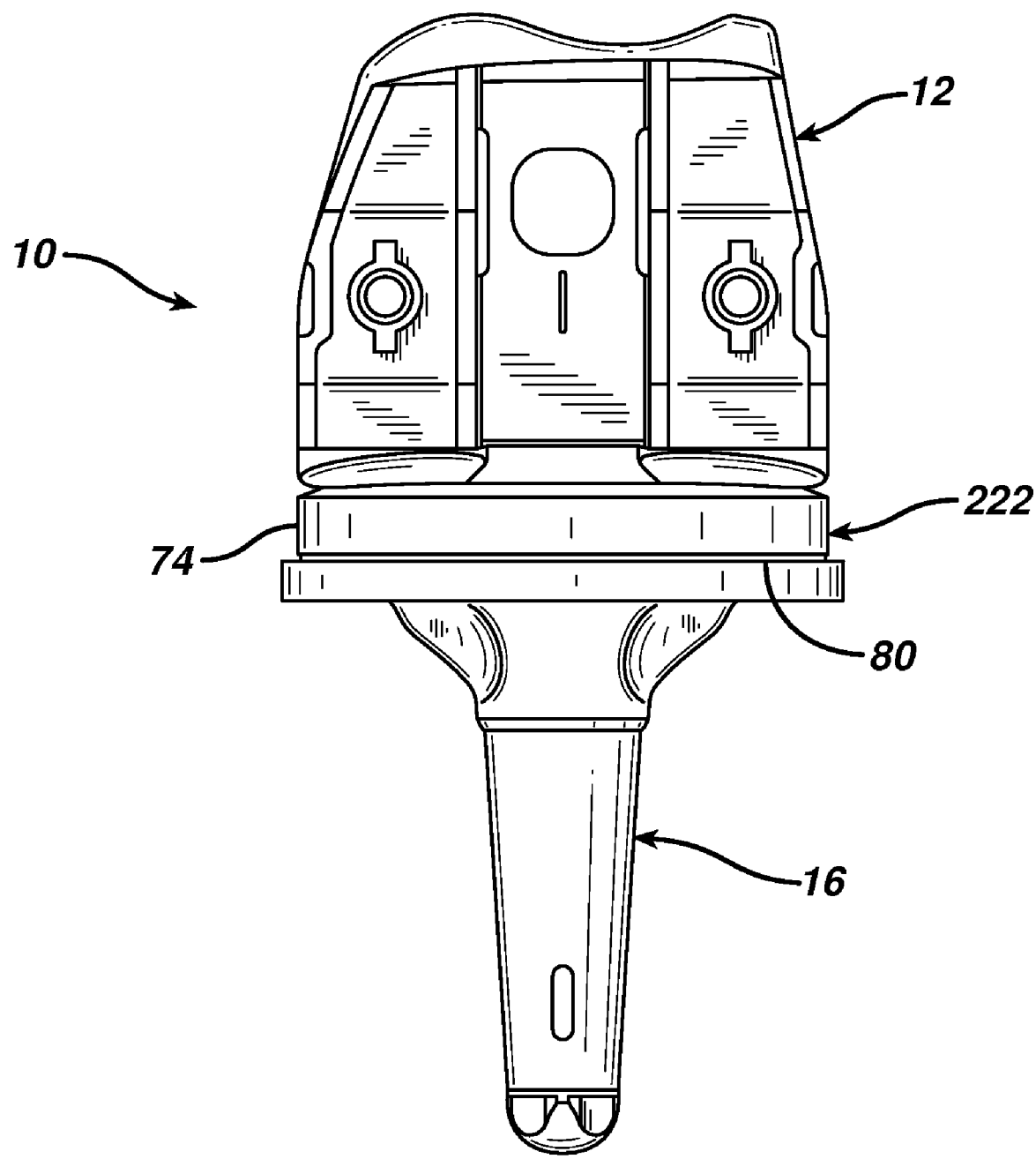
FIG. 24 is an elevation view from the posterior side of the assembly shown in FIGS. 1 and 2 showing the assembly in flexion.

Referring now to FIGS. 21 and 22, one solution to restraining the femoral component 12 with respect to the tibial tray 16 is by the use of a mechanism in the form of a spine 24 located on the bearing component 222 which mates with cam 26 located on femoral component 12. As shown in FIGS. 21 and 22, to provide medial/lateral support for the knee prosthesis 10 preferably the femoral component 12 includes femoral face 30 which cooperate with spine faces 32 on the spine 24. The spine faces 32 define a spine width SW which is related to the femoral width CW defined by femoral faces 32. The relation behind SW & CW define the level of constraint in the prosthesis in the medial-lateral direction.

Referring now to FIG. 8, to provide anterior support the spine 24 includes a cam cooperating face 34 with which the spine cooperating face 35 of the cam 26 cooperates (see FIG. 21). It should be appreciated that for patients in which the posterior cruciate is severely damaged or missing the forces on the spine 24 both anterior/posterior and medial/lateral can be quite severe.

Preferably, and as shown in FIG. 8, the bearing component 222 is made of a polymeric material, for example, polyethylene. Preferably, the bearing component 222 is made of UHM-WPE. The bearing component 222 may be further processed to improve the wear properties of contact surface 40 of the bearing component. The contact surface 40 is the surface that is in contact with the laterally spaced condylar outer periphery 42 of the femoral component 12. Methods of improving the wear properties of UHMWPE include a process known as Gamma Vacuum Foil (GVF) as disclosed in U.S. Pat. No. 5,577,368 to Hamilton, et al, and a process known as the Marathon® process as disclosed in U.S. Pat. No. 6,017,975 and U.S. Pat. No. 6,242,507 to Saum et al and in U.S. Pat. No. 6,228,900 to McKellop et al. These patents are incorporated herein by reference.

Referring again to FIG. 8 and according to the present invention, the bearing component 222 of the prosthesis 10 includes a first component or reinforcing component 236. The reinforcing component 236 serves to strengthen the bearing component 222 so that the spine 24 may withstand the forces that are present in the spine of the knee prosthesis 10 when the posterior cruciate and collateral ligaments cannot support the knee properly.

Since the bearing component 222 is preferably made of a polymer and since the reinforcing component 236 is to strengthen the bearing component 222, the reinforcing component 236 is preferably made of a higher strength material than polymer, preferably a material with a higher modulus of elasticity. For example, the reinforcing component 236 may be made of a metal that is a material compatible with the human anatomy, for example, stainless steel, a titanium and its alloys or a cobalt-chromium-molybdenum alloy.

Applicants have found that desired kinematics of the knee during a full range of motion may require that an optimum design of the components that comprise a knee prosthesis, for example, those of FIG. 8, may include a tibial tray 16 having a central pivot axis 44 which is not coincident with center line 46 of the spine 24 of the bearing component 222. Since the prosthesis 10 including the bearing component 222 will be implanted into the human body, it is essential that the prosthesis 10 including the bearing component 222, be sterilized. Several effective methods of sterilization are possible for the prosthesis 10 including the bearing component 222.

For example, the bearing component 222 may alternatively be sterilized by subjecting the bearing component 222 to gamma irradiation. The subjection of the bearing component 222 to gamma irradiation may lead to the presence of free radicals within the polymer or polyethylene with which the bearing component 222 is typically manufactured. The presence of free radicals within the bearing component 222 may lead to early degradation of the bearing component 222 through an oxidation process.

To minimize the negative effect of the free radicals generated from gamma sterilization, the bearing component 222 preferably is barrier packaged in vacuum or inert gas to keep the oxygen out and also to trap hydrogen gas inside the package. Such treatment precludes early oxidation of the bearing material and sufficient sterilization for the bearing component 222.

According to the present invention, a preferred method of sterilization is gas plasma sterilization. Gas plasma sterilization is predominantly a surface sterilizing technology. Gas plasma sterilization has limited ability to sterilize internal surfaces which have limited exposure to the outer surfaces of the component.

Therefore, and according to the present invention, there is the need for a bearing component designed to be amenable to gas plasma sterilization and yet have the reinforced spine necessary for use of a constrained mobile bearing knee prosthesis for use with patients having compromised or sacrificed cruciate ligaments.

According to the present invention and now referring to FIGS. 15 through 19, an embodiment of the present invention is shown as bearing component 222.

Figure 19:
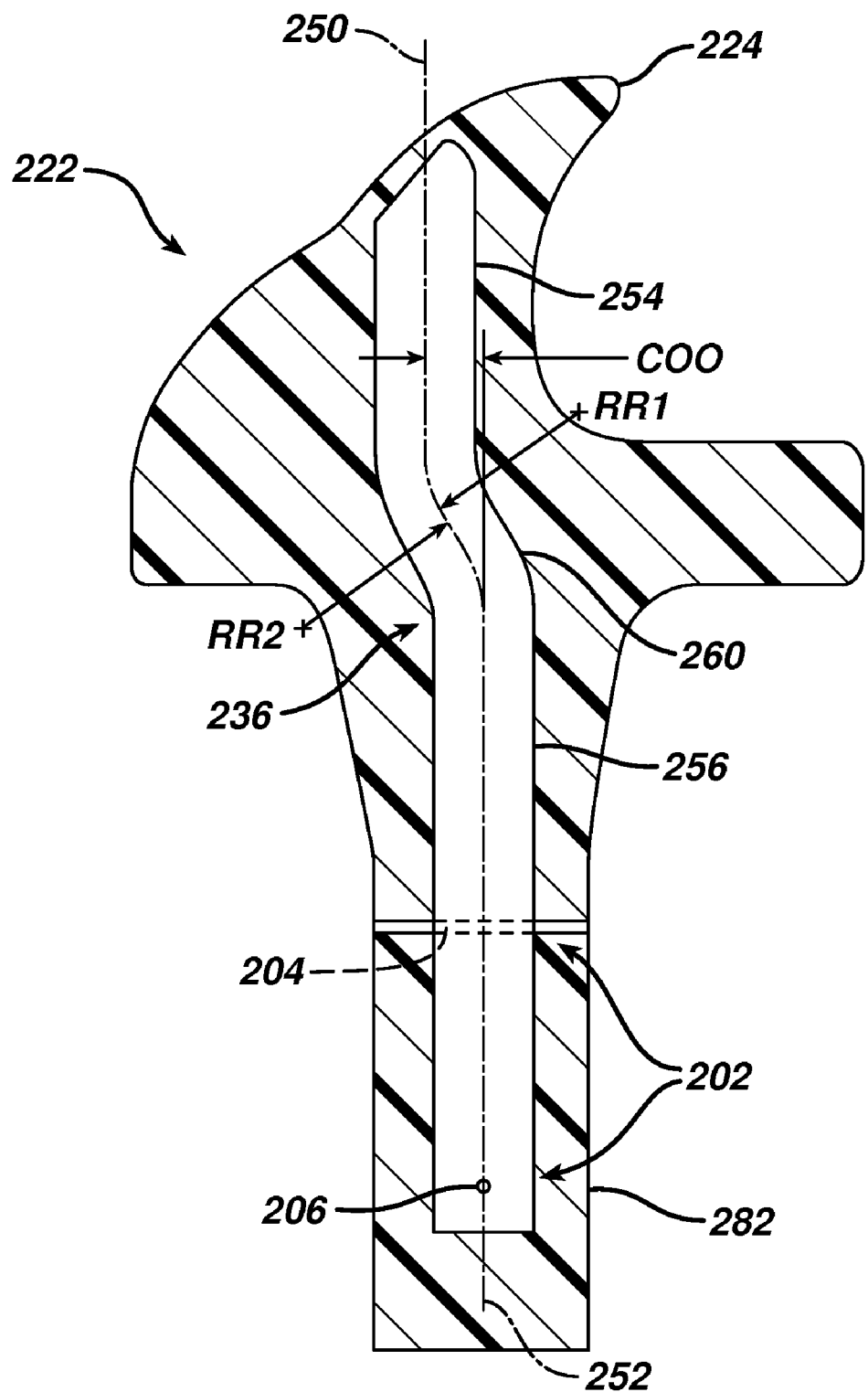
FIG. 19 is a plan view of the bearing component made from the reinforcing rod of FIG. 15 utilizing the molding die of FIG. 16.

Referring now to FIG. 19, the bearing component 222 of the present invention is shown in greater detail. The bearing component 222 is a component that may be molded as a net shaped molding including a reinforcing component or reinforcing rod 236 to provide sufficient strength for the spine 224 and the distal stem. The reinforcing rod includes a first end 286 and an opposed second end 294. The bearing component 222 is designed to not include bearing component openings in the polyethylene portion of the bearing component to expose the reinforcing rod to atmosphere. The technology that permits this configuration will be described in greater detail herein.

By providing the bearing component 222 with no external exposure to the reinforcing rod, the bearing component 222 may be gas plasma sterilized. By gas plasma sterilizing the bearing component 222, the bearing component 222 may be sterilized without providing free radicals which could lead to oxidative degradation of the bearing material.

Referring now to FIG. 19 and according to the present invention, the bearing component 222 of the prosthesis 10 includes the reinforcing component 236 which is designed to accommodate the fact that centerline 44 of the central pivot stem of the tibial tray 16 (see FIG. 8) and is offset from centerline 46 of the spine 24.

Thus, as shown in FIG. 19, the reinforcing component 236 is designed with a first centerline 250 which is not coincident with second centerline 252. As shown in FIGS. 8 and 10, the first centerline 250 of the reinforcing component 236 is coincident with central pivot stem centerline 44 of tibial tray 16. Similarly the second centerline 252 of the reinforcing component 236 is coincident with the centerline 46 of the spine 24.

Continuing to refer to FIG. 19, the reinforcing component 236 includes a first portion 254 which defines the first centerline 250 thereof. The reinforcing component 236 further includes a second portion 256 thereof which defines the second centerline 252 thereof. The first centerline 250 and the second centerline 252 are non-coincidental.

As shown in FIG. 19, the first centerline 250 may be parallel and spaced from the second centerline 252. It should be appreciated, however, that the first centerline 250 and the second centerline 252 may, in fact, be skewed or converging or diverging. As shown in FIG. 19, however, the first centerline 250 and the second centerline 252 are separated and offset a distance COO which is similar to the offset SOO between the centerline of 46 of spine 24 and the centerline 44 of the tibial tray 16 (see FIG. 8).

As shown in FIG. 19, the reinforcing component 236 includes a connecting portion 260 positioned between first portion 254 and second portion 256. The connecting portion 260 may have any suitable shape but preferably for strength and simplicity the connecting portion 260 is an arcuate portion. In such a configuration, the shape of the connecting portion 260 is defined by a pair of radii, RR1 and RR2 which may, for example, be similar.

Figure 15:
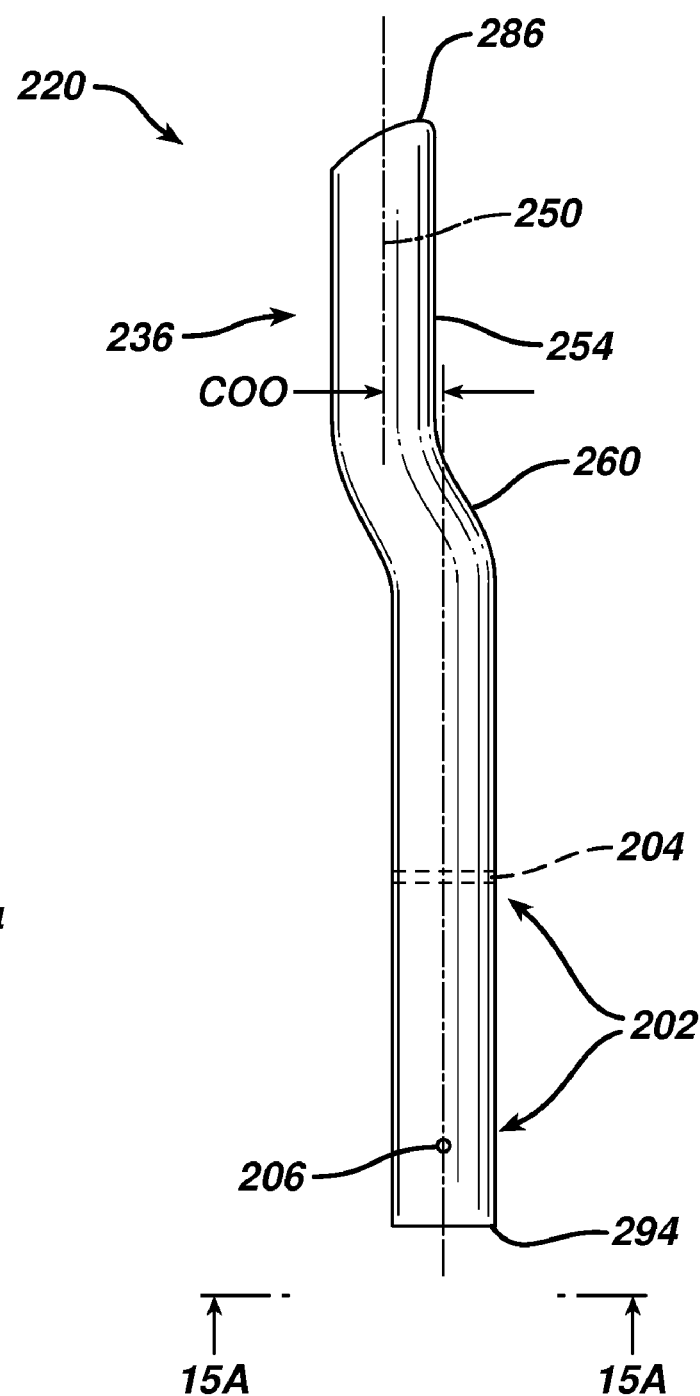
FIG. 15 is a plan view of a reinforcing rod for use with the bearing component for another embodiment of the prosthesis of the present invention.
Figure 15A:
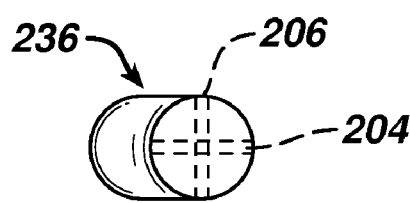
FIG. 15A is a view of the reinforcing rod of FIG. 10 along the line 15A-15A in the direction of the arrows.
Figure 16:
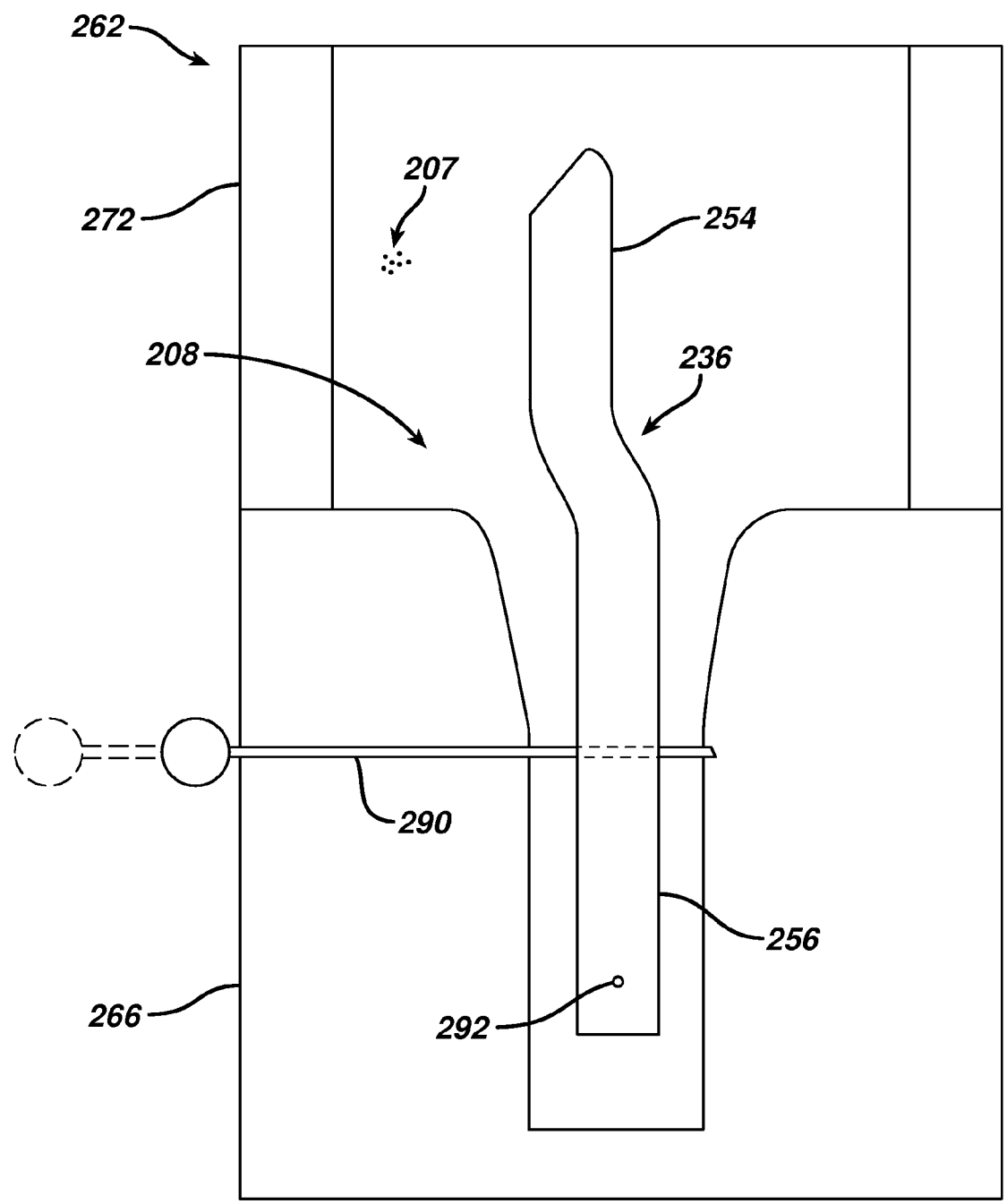
FIG. 16 is a plan view of the reinforcing rod of FIG. 15 located in a molding die for use in manufacturing the bearing component for the prosthesis of the present invention.

While it should be appreciated that the reinforcing component 236 may have any suitable shape capable of providing for support with a pair of offset centerlines, it should be appreciated that for simplicity, and as shown in FIG. 15A, the reinforcing component 236 may have a uniform cross section. For example, the cross section of the reinforcing component may be square, triangular, hexagonal or as shown in FIG. 15A, may be circular. A circular cross section may provide for optimum bending strength in a variety of directions for a given weight or size of the reinforcing component 236.

Figure 18:
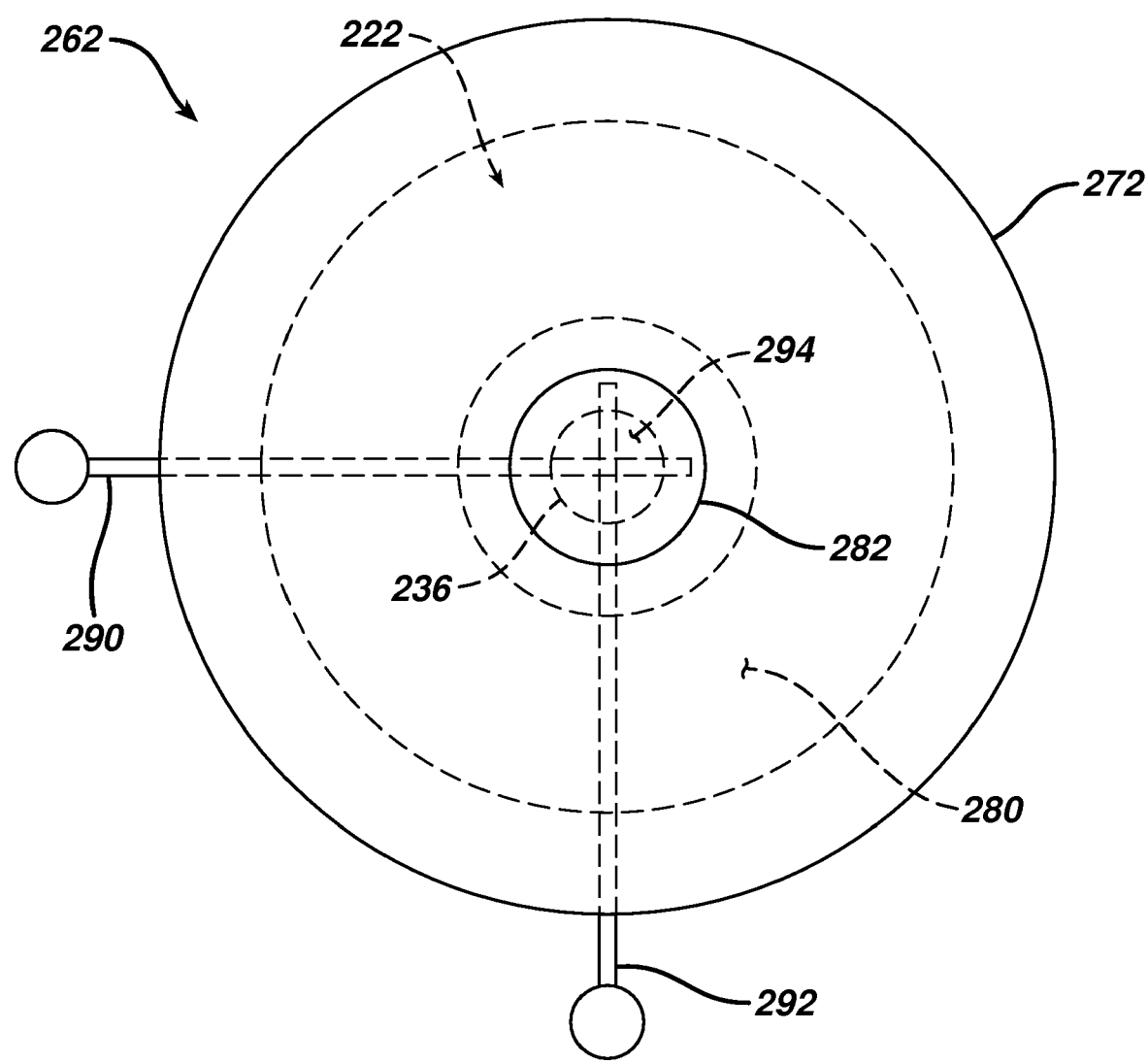
FIG. 18 is a bottom view of the molding die of FIG. 16.

The reinforcing component 236 may be hollow or as shown in FIG. 18, may be made of a generally solid material. Due to space constraints, the reinforcing component 236 may be solid as shown in FIG. 18.

As can be readily apparent by FIGS. 15 and 19, in particular, the bearing component 222 including the reinforcing component 236 may be made by a number of methods but cannot simply and easily be made by first making the bearing component 222 and then preparing an opening or conduit for installing the reinforcing component 236 therein. Therefore, typical methods of providing a reinforcing rod to a bearing component 222 in the form of drilling a hole in the bearing component 222 and inserting a straight cylindrical rod therein is not possible.

Referring now to FIG. 19, the reinforcing component or reinforcing rod 236 is shown in greater detail. The bearing component 222 includes the reinforcing rod 236 which is placed into a mold and the polymeric material is molded around the reinforcing rod 236. Thus, the bearing component 222 requires that the mold provide provisions for the proper placement of the reinforcing rod 236 within the molding die. Therefore, and as shown in FIG. 19, the reinforcing rod 236 includes an orientation and location feature 202 which provides both orientation and location. The location and orientation feature 202, as shown in FIG. 15, include a first recess or through hole 204 and a second recess or through hole 206.

Preferably, the first recess 204 and the second recess 206 are small. The first recess and second recess 204 and 206 in the reinforcing rod 236 are preferably both located on the same portion of the rod. By placing the recesses on the same portion, for example second portion 256, the recesses may be both positioned in the base or bottom mold 266 of the die 262 (see FIG. 17) to assist in the proper operation of the invention.

The value of having the recesses on the same end of the rod will be described in greater detail herein.

Figure 17:
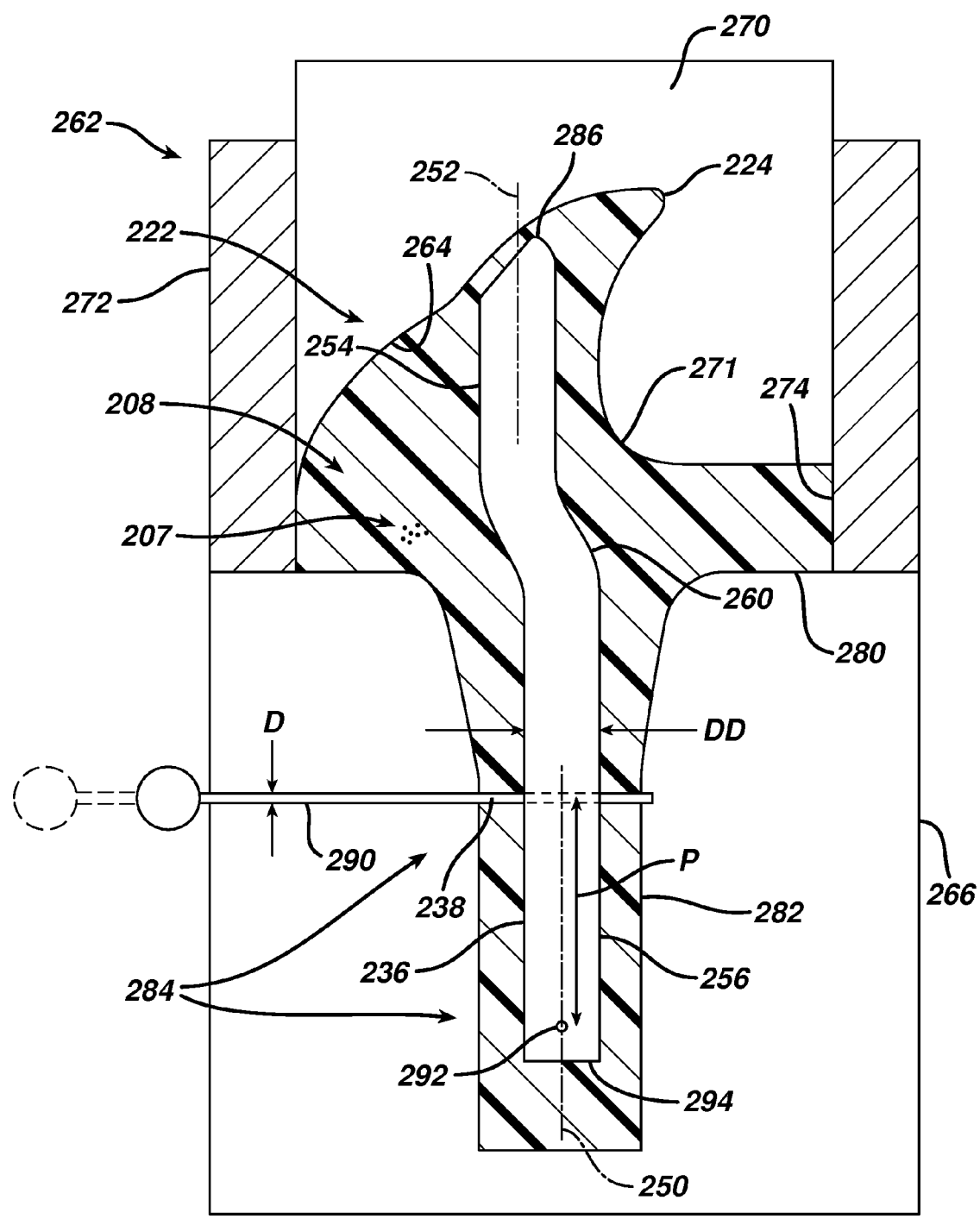
FIG. 17 is a plan view of the reinforcing rod of FIG. 15 located in a molding die shown partially in cross section for use in manufacturing the bearing component for the prosthesis of the present invention showing the molding die in greater detail.

Referring now to FIG. 17, a molding die 262 is shown for molding the bearing component 222. Molding die 262 is utilized in the direct compression molding process. The bearing component 222 is molded in the molding die 262 in reverse or upside down order to provide for the positioning of the recesses 204 and 206 in the base or bottom mold 266.

The advantage of positioning the location and orientation features 202 in the base or bottom mold 266 will be described in greater detail later.

As shown in FIG. 17, the molding die 262 includes base or bottom mold 266. The bottom mold 266 is utilized to form bottom bearing surface 280 and rotating shaft or second peripheral region 282 of the bearing component 222. Extending upwardly from the bottom mold 266 is the body or side mold 272. The side mold 272 is utilized to form curved profile 274 of the bearing component 222. Slidably positioned within the side mold 272 is plunger or top mold 270. The plunger or top mold 270 is utilized to form articular surface or first peripheral region 271 of the bearing component 222. The molds 270, 272 and 266 serve to provide an inner forming surface 264 which conforms to the outer periphery of the bearing component 222 with provisions for accommodating the shrinkage dimensions that are well known in the art.

The inner forming surface 264 defines an internal cavity 208.

The reinforcing rod 236 needs to be properly positioned within the cavity 208 of the molding die 262. Preferably, thus, the molding die 262 includes a positioner 284 for proper repositioning of the reinforcing rod 236 within the cavity 208 of the molding die 262. For example and as shown in FIG. 17, the positioner 284 is in the form of a first pin 290 and a second pin 292. The pins 290 and 292 cooperate with first recess 204 and second recess 206 of the reinforcing rod 236 (see FIG. 19).

Preferably, and according to the present invention, the pins 290 and 292 have a very small dimension with respect to the reinforcing rod 236. For example, if, as shown in FIG. 17, the pins 290 and 292 are cylindrical, the pins 290 and 292 may have a diameter D which is much smaller than diameter DD of the second portion 256 of the reinforcing rod 236. For example for a reinforcing rod 236 having a diameter DD of, for example, approximately 10 millimeters. The corresponding diameter D of the pins 290 and 292 may be, for example, 0.5 to 2.0 millimeters.

It is preferred to have the pins 290 and 292 made of materials that have a high melting point in order to resist the heat and pressure experienced in the mold during the molding process. Pins may be made of metals, ceramics or pyrolytic carbons. The molding process for the molding die 262 to mold the bearing component 222 as shown in FIG. 17 includes first separating the top mold 270 from the bottom mold 266 and adding powder 207 similar to powder 112 of the process as described for the molding die 62 of FIG. 12. After the required powder 207 is added, the top mold 270 is placed within the side mold 272 and lowered in the direction of the bottom mold 266 until the molds 266, 270 and 272 forming surface 264 correspond to the periphery of the bearing component 222.

Towards the end of the compression molding cycle when the UHMWPE material has almost assumed full density and completely fills the mold the pins 290 and 292 are withdrawn from the cavity preferably in a direction normal to the centerlines 250 and 252 of the reinforcing rod 236. For example, as shown in FIG. 17, the first pin moves from a position as shown in solid to the position shown in phantom. As the first pin 290 and second pin 292 are retracted to the position in phantom, a small pin cavity 238 is left behind where the pin 290 was withdrawn from. Since the compression cycle has not ended, the melted polymer still under pressure quickly fills the pin cavity 238 thereby eliminating the pin cavity 238.

Since the powder 207 within the mold cavity 208 has obtained a high viscosity at the point in the compression molding cycle when the UHMWPE material has assumed full density and completely fills the mold, the reinforcing rod 236 remains in its previous position even after the pins 290 and 292 have been fully retracted and no longer support the rod 236.

Preferably, and as shown in FIG. 17, the pins 290 and 292 are preferably spaced apart along second centerline 250 a distance P of, for example, twice the distance DD of the diameter of the rod 236. The larger the dimension P, the greater the stability and accuracy of the positioning of the rod 236 within the molding die 262.

Preferably, and as shown in FIG. 17, the pins 290 and 292 are positioned perpendicularly to the second centerline 250 and preferably at an angle with respect to each other, preferably at 90 degrees or perpendicular to each other. Such positioning optimizes the effectiveness of the pins 290 and 292 to properly position the reinforcing rod 236 in more than 3 degrees of freedom. After appropriate cooling, the plunger or top mold 270 is opened and the completed bearing component 222 is removed from the molding die 262.

It should be appreciated that other approaches may be taken to position the reinforcing rod 236 within the molding die 262 and yet provide for a complete encapsulation of the reinforcing rod with the polyethylene. For example, the pins 290 and 292 may be made of a polyethylene identical to that of the powder 207. The pins 290 and 292 may then be left fully extended and not retracted. The pins 290 and 292 then would melt and form with the powder 207, and yet have sufficient strength early on in the forming process to properly locate the rod 236 within the molding die 262 until the polyethylene becomes sufficiently viscous to support the rod.

Other approaches for properly supporting the rod yet allowing for complete encapsulation of polyethylene around the rod 236 may fall within the scope of the present invention.

According to the present invention and now referring to FIGS. 10 through 14, another embodiment of the present invention is shown as bearing component 22.

Referring to FIG. 8 it should be appreciated that the bearing component 22 of FIG. 10 may be substituted for the bearing component 222 for the prosthesis 10. The bearing component 22 is made of similar materials and has similar strength and load carrying capacity of bearing component 222 as well as similar contour dimensions such that bearing component 22 can readily replace bearing component 222 in the prosthesis 10.

Referring now to FIG. 10 an alternate embodiment of the bearing component of the present invention is shown as the bearing component 22 which may alternatively be used in prosthesis 10. Bearing component 22 includes the reinforcing component 36 which is designed to accommodate the fact that centerline 44 of the central pivot stem of the tibial tray 16 is offset from centerline 46 of the spine 24 (see FIG. 8). Thus as shown in FIG. 10, the reinforcing component 36 is designed with a first centerline 50 which is not coincident with second centerline 52. As shown in FIGS. 8 and 10, the first centerline 50 of the reinforcing component 36 is coincident with central pivot stem centerline 44 of tibial tray 16. Similarly the second centerline 52 of the reinforcing component 36 is coincident with the centerline 46 of the spine 24.

Continuing to refer to FIG. 10, the reinforcing component 36 includes a first portion 54 which defines the first centerline 50 thereof. The reinforcing component 36 further includes a second portion 56 thereof which defines the second centerline 52 thereof. The first centerline 50 and the second centerline 52 are non-coincidental.

As shown in FIG. 10, the first centerline 50 may be parallel and spaced from the second centerline 52. It should be appreciated, however, that the first centerline 50 and the second centerline 52 may, in fact, be skewed or converging or diverging. As shown in FIG. 10, however, the first centerline 50 and the second centerline 52 are separated and offset a distance CO which is similar to the offset SO between the centerline of 46 of spine 24 and the centerline 44 of the tibial tray 16 (see FIG. 8).

As shown in FIG. 10, the reinforcing component 36 includes a connecting portion 60 positioned between first portion 54 and second portion 56. The connecting portion 60 may have any suitable shape but preferably for strength and simplicity the connecting portion 60 is an arcuate portion. In such a configuration, the shape of the connecting portion 60 is defined by a pair of radii, R1 and R2 which may, for example, be similar.

While it should be appreciated that the reinforcing component 36 may have any suitable shape capable of providing for support with a pair of offset centerlines, it should be appreciated that for simplicity, and as shown in FIG. 10A, the reinforcing component 36 may have a uniform cross section. For example, the cross section of the reinforcing component may be square, triangular, hexagonal or as shown in FIG. 10A may be circular. A circular cross section may provide for optimum bending strength in a variety of directions for a given weight or size of the reinforcing component 36.

The reinforcing component 36 may be hollow, or as shown in FIG. 10A may be made of a generally solid material. Due to space constraints the reinforcing component 36 may be solid as shown in FIG. 10A.

As can be readily apparent by the FIGS. 8 and 10, in particular, the bearing component 22, including the reinforcing component 36, may be made by a number of methods but cannot simply and easily be made by first making the bearing component 22 and then preparing an opening or conduit for installing the reinforcing component 36 therein. Therefore, typical methods of providing a reinforcing rod to a bearing component 22 in the form of drilling a hole in the bearing component 22 and inserting a straight cylindrical rod therein is not possible.

Figure 11:
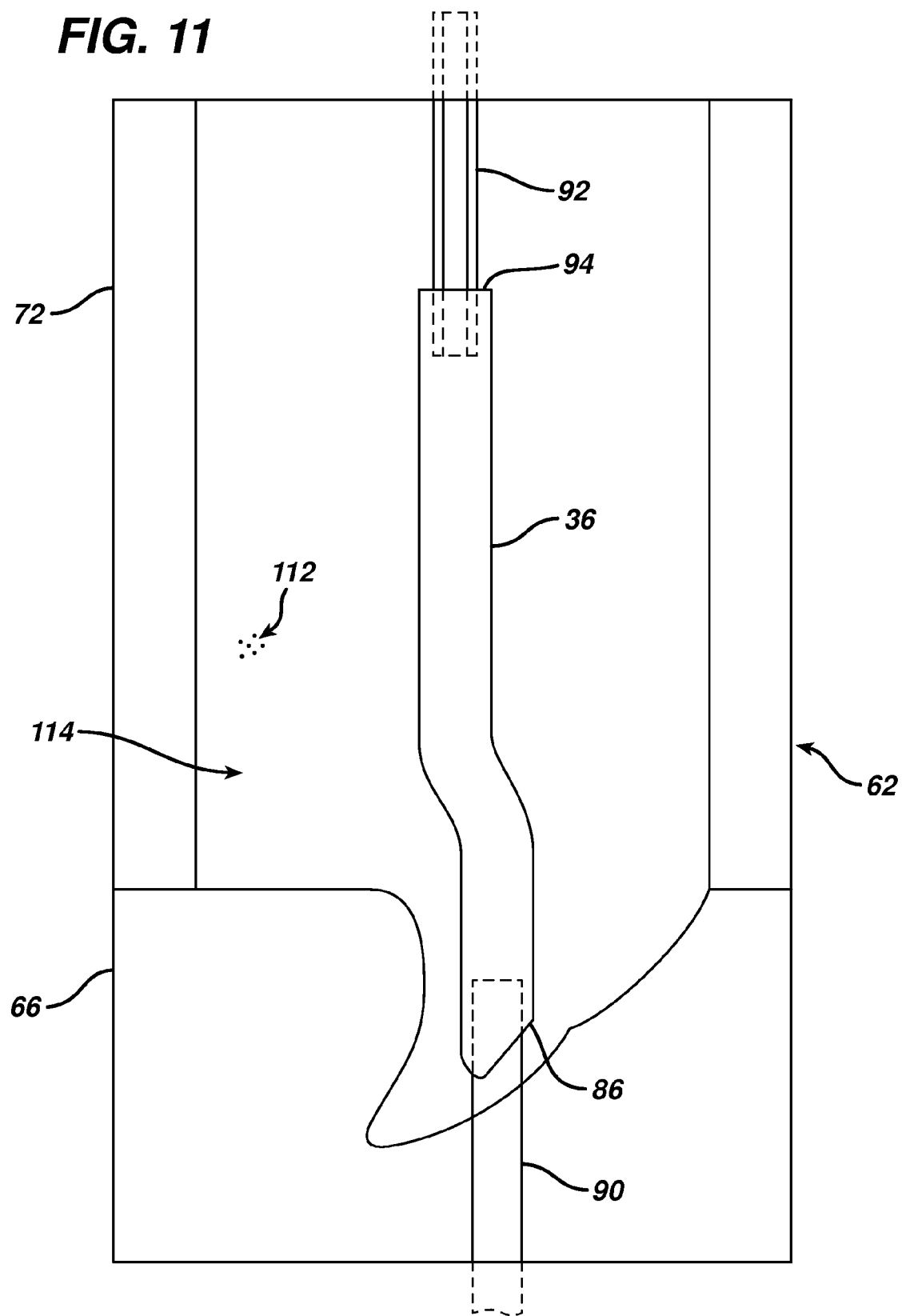
FIG. 11 is a plan view of the reinforcing rod of FIG. 10 located in a molding die for use in manufacturing the bearing component for the prosthesis of the present invention.
Figure 12:
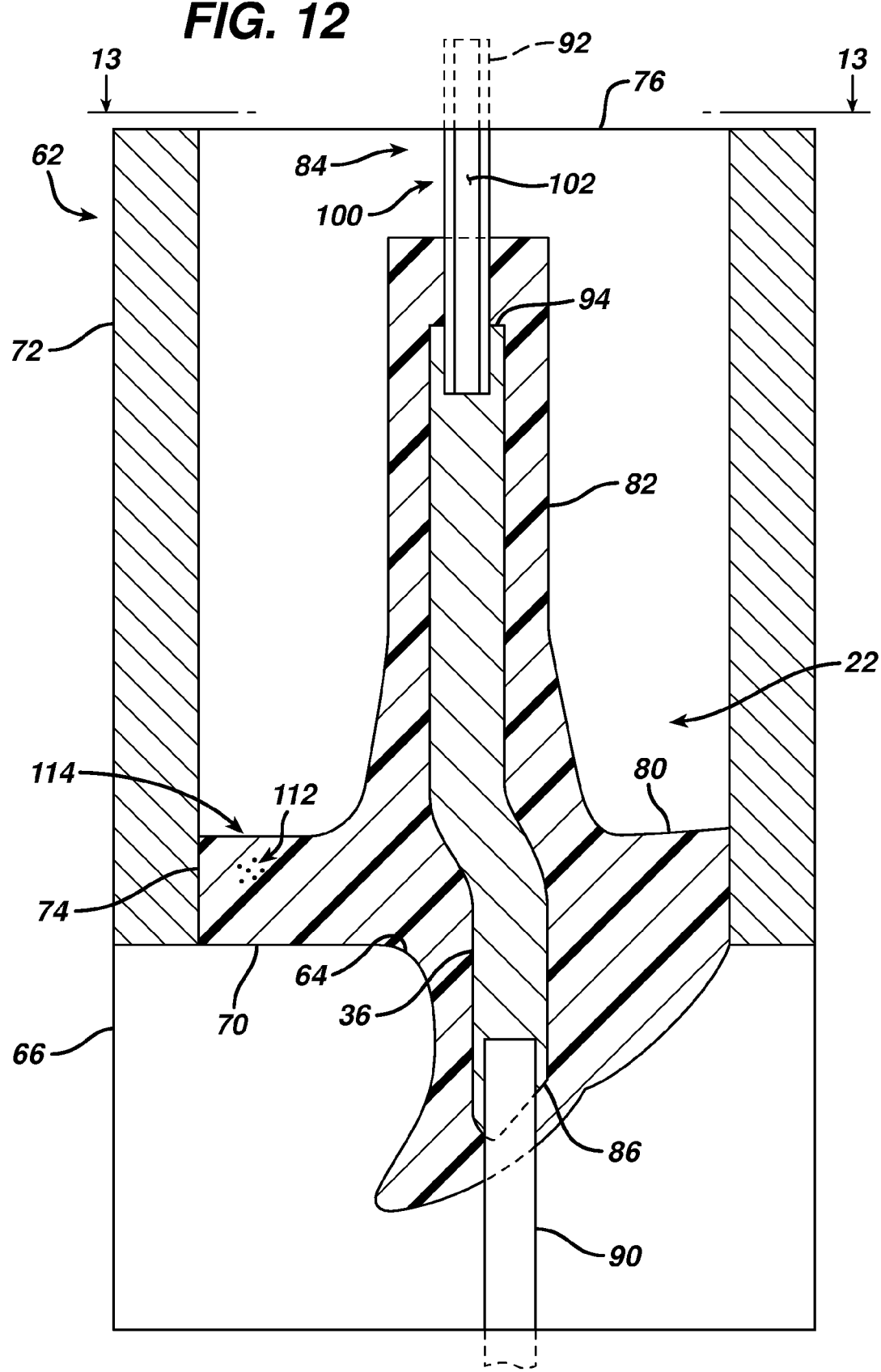
FIG. 12 is a plan view of the reinforcing rod of FIG. 10 located in a molding die shown partially in cross section for use in manufacturing the bearing component for the prosthesis of the present invention showing the molding die in greater detail.
Figure 13:
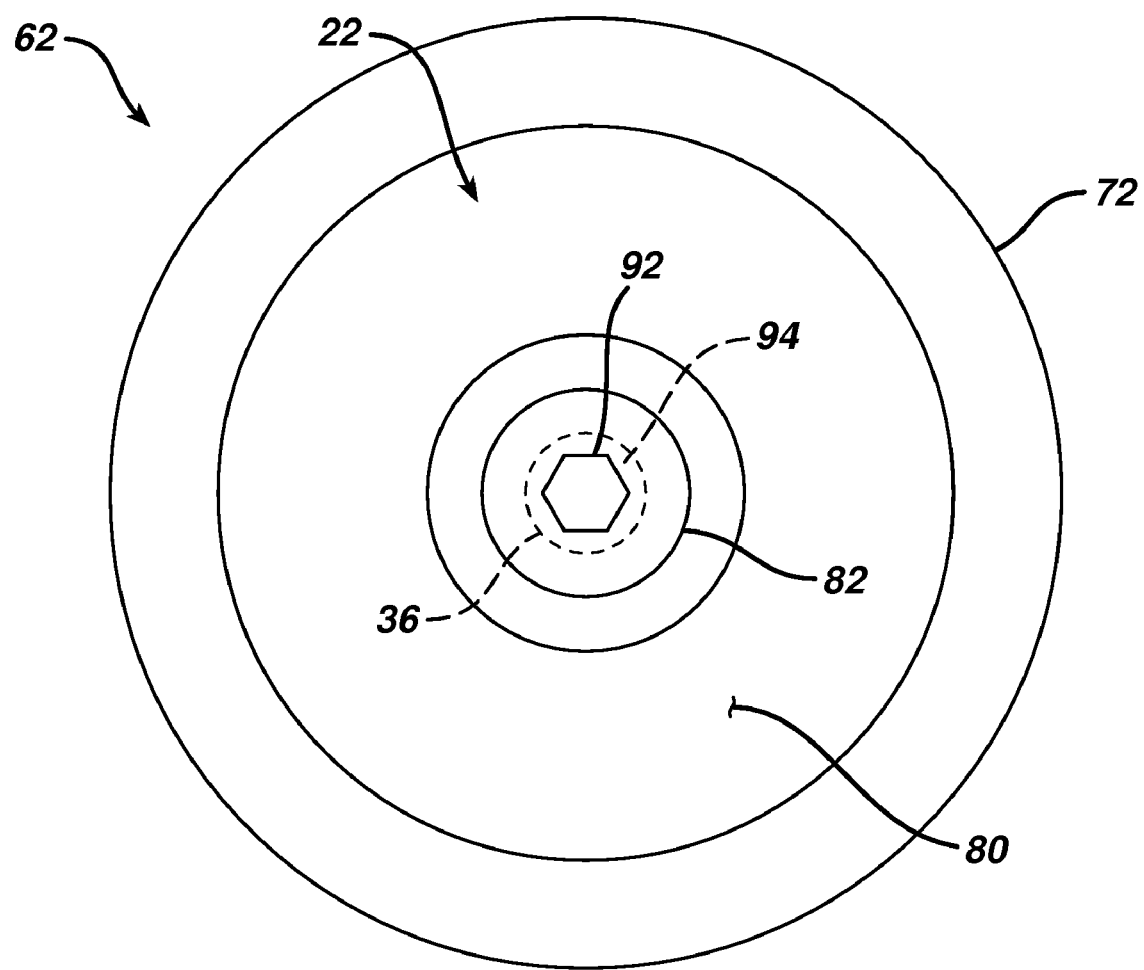
FIG. 13 is a bottom view of the molding die of FIG. 12.

Therefore, referring to FIGS. 11, 12 and 13, the bearing component 22 is preferably made by a molding process for example a compression molding process or any molding process by which the polymeric material may be processed.

Referring to FIGS. 11, 12 and 13, the bearing component 22 is preferably made in molding die 62. While the bearing component 22 may be manufactured utilizing any suitable molding technique preferably and as shown in FIG. 12, the molding die 62 is for use with direct compression molding. Plastic powder is placed into the molding die 62, the die is closed and pressure is applied to compress, heat, and cause flow of the plastic to be conformed to the cavity shape.

The molding die 62 is made in a shape including an inner forming surface 64 which is made in the shape of the final finished bearing component 22. Preferably, the inner forming surface 64 is sized to allow for appropriate shrinking dimensions as is known in the art.

The molding die is made in several pieces. Typically, a base or bottom mold 66 is utilized to form articular surface 70 of the bearing component 22. The molding die 62 also includes a body or side mold 72. The body 72 is utilized to form the curved lateral surfaces 74 of the bearing component 22. Also the molding die 62 further includes a plunger assembly 76. The plunger assembly 76 is utilized to form bottom bearing surface 80 and the rotating shaft 82. One mold may be used to obtain varying thickness of the bearing component 22.

In order to manufacture the bearing component 22 according to the present invention, the molding die 62 is modified to support reinforcing component 36 in the form of, for example, a reinforcing rod.

Preferably, and as shown in FIG. 12, reinforcing rod or component 36 is position spaced from the inner forming surface 64. Preferably, and as shown in FIG. 12, the reinforcing rod 36 is kept spaced from the inner forming surface 64 by use of a support feature 84 as initially designed to provide the offset between the spine and distal stem of the bearing component 22. The support feature 84 is utilized to space, support or position the reinforcing rod 36 within the molding die 62. The positioner or support feature 84 may support or secure the reinforcing component 36 at any suitable position on the reinforcing component 36. For simplicity, and as shown in FIG. 12, the positioner 84 may be located on first end 86 of the reinforcing rod 36.

The positioner 84 may include a sole positioning member which interacts with first end 86 of the reinforcing rod 36. If the positioner is located only on one end and the rod is held at that one end, that portion of the die including the positioner either at the base or bottom mold 66 or the plunger or top mold 76 must provide rigid temporary attachment of the reinforcing rod 36 to the positioner 84.

While the present invention may be practiced utilizing a sole positioner located on one end of the reinforcing rod 36 such a configuration may have some problems in that the tolerance between the positioner and the reinforcing rod may be such that the accuracy of the position of the reinforcing rod 36 within the molding die 62 may not be sufficiently accurate resulting in the misposition of the reinforcing rod 36 within the finished reinforcing component 36. Misposition may occur either in the anterior-posterior or medial-lateral direction. Additionally, the reinforcing pin 36 may be rotationally mispositioned with respect to the superior spine and distal stem.

Preferably, and as shown in FIG. 12, the positioner 84 is in the form of a first positioner 90 located at the first end 86 of the reinforcing rod 36 and a second positioner 92 located at second end 94 of the reinforcing rod 36. If the reinforcing rod 36 is held at both the first end 86 and the second end 94 of the rod 36, then one end, for example, end 86 must be a rigid temporary attachment and the other end, for example, second end 94 or second positioner 92 must be a sliding temporary attachment. A sliding temporary attachment is necessary as the two ends of the molding die approach and separate from each other during each molding cycle. Additionally, the sliding temporary attachment may provide for rotational alignment to obtain the optimal position of the reinforcing component 36 in the spine by allowing equal polymeric material around the reinforcing component 36.

To improve the accuracy of the positioning of the reinforcing rod 36 within the molding die 62, optionally, the molding die may include an orientation feature 100 to optimally angularly orient the reinforcing rod 36 with respect to the inner forming surface 64 and eventually the reinforcing component 36. The orientation feature 100 may, for example, be included with the positioners 90 and 92 and may, as shown in FIG. 12, be in the form of flat 102 located on the second positioner 92. As shown in FIG. 12, the orientation feature 100 is in the form of six equally spaced flats, three of which are shown. Therefore the positioner 84 and the orientation features are in the form of a hexagonal rod. An additional flat may help better fine tune the position of the reinforcing element with respect to the mold components.

Referring again to FIG. 10, preferably, and as shown in FIG. 10, the reinforcing rod 36 includes positioning features in the form of, for example, first recess 104 which is located on first end 86 of the rod 36 and second recess 106 which is located on second end 94 of the rod 36. The first recess 104 matingly receives the first positioner 90 while the second recess 106 receives the second positioner 92 (see FIG. 11). Preferably, and as shown in FIG. 10, the second recess 106 includes a recess flat 110 which mate with flat 102 on second positioner 92.

Figure 14:
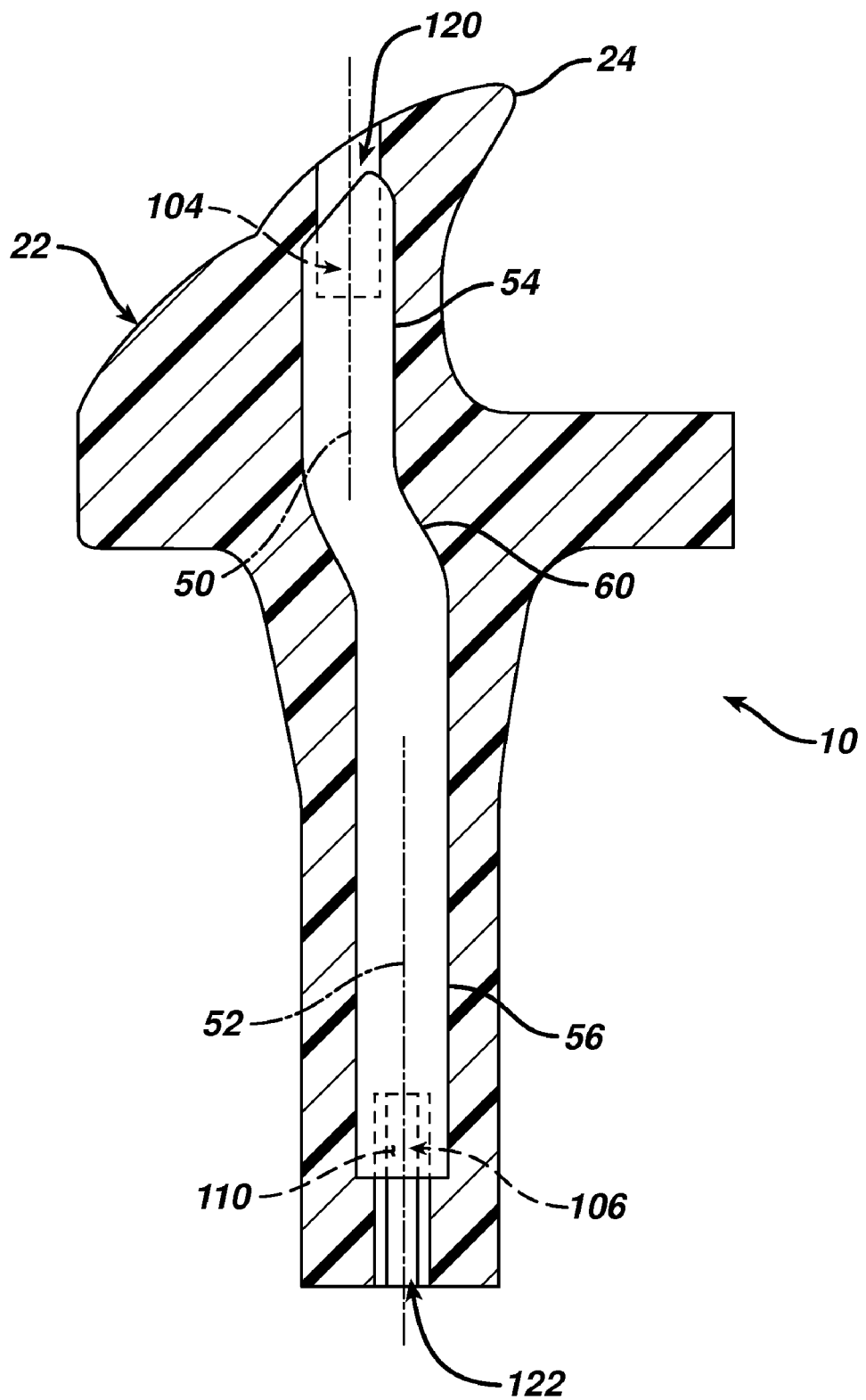
FIG. 14 is a plan view of the bearing component made from the reinforcing rod of FIG. 10 utilizing the molding die of FIG. 12.

Referring now to FIG. 14, the bearing component 22 is shown having been molded on the molding die 62 (see FIG. 12). In order that the first positioner 90 and the second positioner 92 may be removed from the cavity 114 and from the bearing component 22 when it is removed from the cavity 114 of the molding die 62, the bearing component 22 includes a first bearing component opening 120 located in line and above the first recess 104 of the reinforcing rod 36. Likewise, the bearing component 22 further includes a second bearing component opening 122 extending outwardly from the second recess 106 of the reinforcing rod 36. The first bearing component 120 and the second bearing component opening 122 provide for access to the reinforcing rod 36 from the outside of the bearing component 22.

Referring again to FIG. 12, plastic powder 112 is added in the proper amount into cavity 114 of the molding die 62. The molding die 62 is closed by the positioning of the plunger assembly or top mold 76 over the body or side mold 72 of the molding die 62.

The bearing component 22 is fully formed by subjecting the molding die 62 to the well known conditions of pressure and temperature required to consolidate the powder 112. After appropriate cooling, the molding die 62 is opened by the removal of the plunger assembly or top mold 76 from the body or side mold 72. The bearing component 22 including the reinforcing rod 36 is then removed from the cavity 114 of the molding die 62. After proper cleaning an additional reinforcement rod and additional powder 112 is added to the cavity 114 and the process is repeated in order to obtain a second bearing component.

Referring now to FIG. 14, the bearing component 22 of the present invention includes first bearing component opening 120 and second bearing component opening 122 which expose the bearing component 22 to access the reinforcing rod 36. The reinforcing rod thus has internal surfaces which have limited exposure or connection to the outside surfaces of the bearing component 22.

Therefore, because the reinforcing rod, 36 is exposed to the surface of the component via the holes 120 and 122 through which it was inserted or by the method of holding the post using the mold which holds the post during the molding process, the bearing component 22 is not amenable to sterilization by techniques which are predominantly surface sterilizing technology, for example, gas plasma sterilization.

In order to utilize the bearing component 22 with gas plasma sterilization, steps can be taken to fill the holes 120 and 122 with polyethylene plugs or the positioners 90 and 92 can be made of polyethylene and not retracted once the bearing 22 is removed from the die 62 (see FIG. 12).

Figure 20:
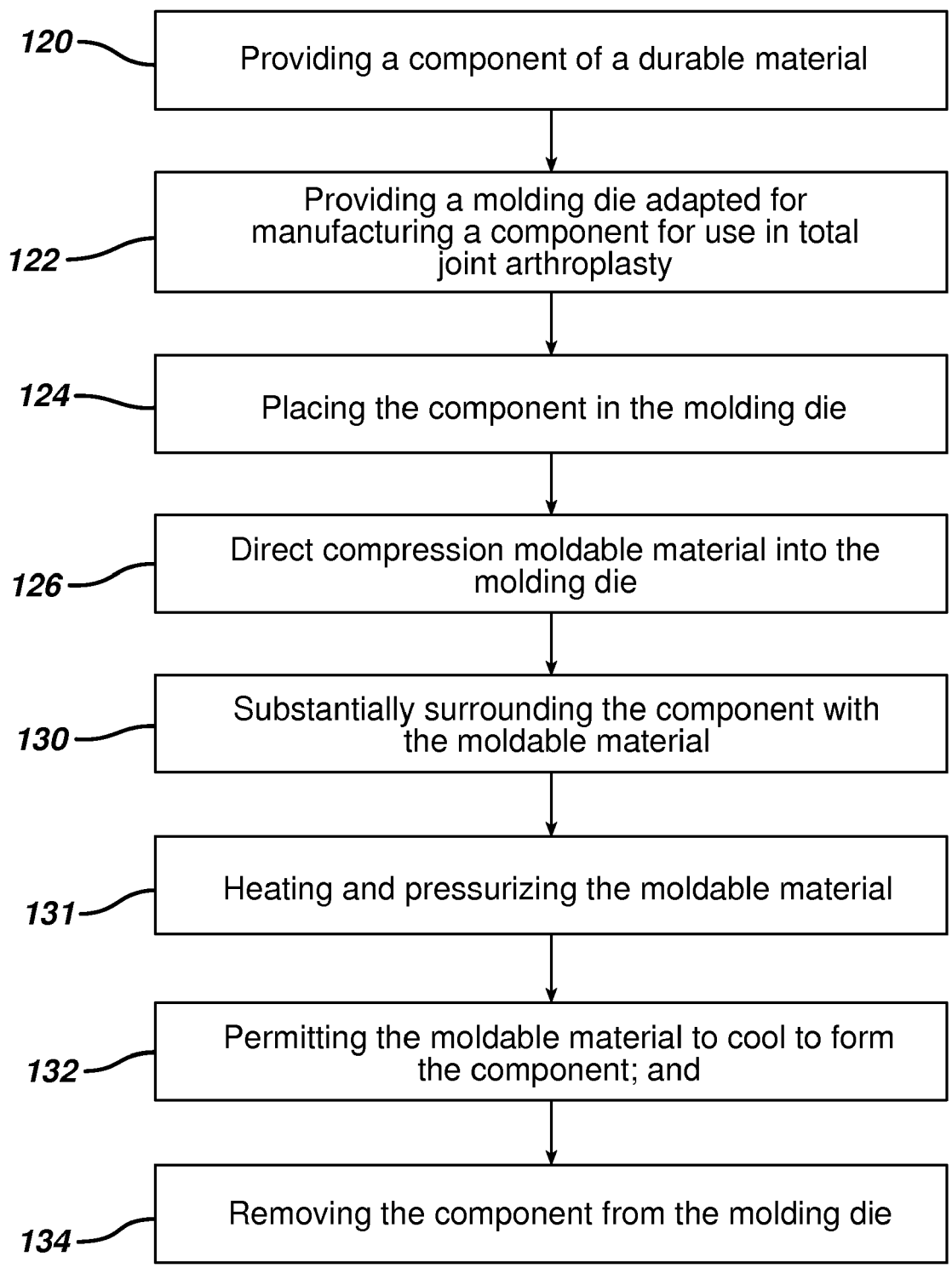
FIG. 20 is a process flow chart for a method of manufacturing the prosthesis component of FIG. 21.

Referring now to FIG. 20, a process for molding a bearing component with a reinforcing rod is described more fully. First step 120 of the process described in FIG. 20 is the step of providing a component of a durable material. The durable material may, for example, be in the form of cobalt chrome alloy, stainless steel or titanium and its alloys. The component may be in the form of, for example, an elongated member, for example, a rod. The rod as described in the present invention is in the form of a bent rod or a rod having two substantially linear portions with the portions being skewed or non-linear with respect to each other.

Second step 122 of the process, as described in FIG. 20, is the step of providing a molding die adapted for manufacturing a component for use in total joint arthroplasty.

Third step 124 in the process is the step of placing the reinforcing component into the molding die in the desired position. Fourth step 126 of the process is placing moldable material powder into the molding die. Fifth step 130 in the process for making a bearing component is the step of substantially surrounding the component with moldable material. Sixth step 131 of the process is the step of heating and pressurizing the mold, thus the moldable material. Seventh step 132 of the process is the step of permitting the moldable material to cool to form the component and the eighth step 134 of the process is the step of removing the component from the molding die.

By utilizing the non-linear reinforcement component of the present invention, a knee may be provided with improved load carrying capacity in the anterior-posterior and medial-lateral directions for the spine and cam mechanism in situations in which the center line of the insert which engages the tibial tray and the superior spine portion which engage the cam of the femoral component are not in the same plane. In such situations where these planes are different, the kinematics of the knee may be improved.

By providing a tibial bearing insert with an insert that has most of its entire periphery encapsulated in polyethylene, a tibial bearing insert can be made that has improved strength and can be gas plasma sterilized.

By providing a non-linear re-inforcing component to the tibial bearing insert, the non-linear support rod may be properly positioned within the tibial bearing insert to optimize the load transfer mechanism through the spine.

By providing a tibial bearing insert including a nonlinear support including an orientation feature, the support rod may be adjusted with respect to the tibial bearing insert during the manufacturing of the tibial bearing insert.

Although the present invention and its advantages have been described in detail, it should be understood that various changes, substitutions, and alterations can be made therein without departing from the spirit and scope of the present invention as defined by the appended claims.

We claim:

1. A knee joint prosthesis, comprising:
a distal femoral implant component for cooperation with a femur, the distal femoral implant component including a cam;
a metal tibial tray implant component for cooperation with a tibia; and
a tibial bearing component positionable between said distal femoral implant component and said tibial tray implant component and cooperable therewith,
said bearing component including a contact surface for contacting the distal femoral implant component, a bottom bearing surface opposite the contact surface for contacting the tibial tray implant component, a spine for cooperation with the cam of the femoral component, a shaft extending out from the bottom bearing surface, an elongate one-piece reinforcing rod having a first end in the spine and a second end in the shaft and a polymeric material defining the spine, the shaft, the contact surface and the bottom bearing surface and completely encapsulating the reinforcing rod and molded thereto, so that the bearing component may be sterilized by a predominately surface sterilizing technology;

said reinforcing rod having a first portion at the first end and a second portion at the second end, the first portion having a first longitudinal centerline and the second portion having a second longitudinal centerline, said reinforcing rod including a plurality of through holes extending transversely to the centerline of at least one of the first portion and the second portion, at least two of the through holes being oriented in a non-parallel relationship.

2. The joint prosthesis of claim 1, wherein the predominately surface sterilizing technology comprises a gas plasma spray process.

3. The joint prosthesis of claim 1, wherein said polymeric material extends normally from the surface of said reinforcing rod a distance of at least 5 millimeters.

4. The joint prosthesis of claim 1, wherein said polymeric material comprises crosslinked ultra high molecular weight polyethylene.

5. The joint prosthesis of claim 1 wherein the first centerline and second centerline are non-coincidental.

6. The joint prosthesis of claim 5 wherein the second centerline is parallel and spaced from the first centerline.

7. The joint prosthesis of claim 1 wherein the reinforcing rod includes four spaced through holes, two of the through holes being in the first portion of the reinforcing rod and two of the through holes being in the second portion of the reinforcing rod.

8. The joint prosthesis of claim 1 wherein two of the through holes are oriented substantially perpendicular to the first centerline and the second centerline and substantially perpendicular to each other.

9. The joint prosthesis of claim 1 wherein the through holes in the reinforcing rod are filled with polymeric material.

10. A tibial bearing comprising a contact surface, a spine extending out from the contact surface, a bottom bearing surface opposite the contact surface, a shaft extending out from the bottom bearing surface, and an elongate one-piece metal reinforcing rod having a first end in the spine and a second end in the shaft, the metal reinforcing rod having a thickness and a plurality of through holes, each hole extending transversely through the thickness of the metal reinforcing rod, at least two of the holes being oriented in a non-parallel relationship, the tibial bearing including a polymeric material defining the spine, the shaft, the contact surface and bottom surface of the tibial bearing and completely encapsulating the metal reinforcing rod and molded thereto, so that the bearing may be sterilized by a predominately surface sterilizing technology, wherein the reinforcing rod comprises a first portion in the spine defining a first centerline thereof, and a second portion in the shaft defining a second centerline thereof, and wherein the through holes in the metal reinforcing component define holding features thereon for holding the reinforcing component when placing the polymeric material onto the reinforcing component.

11. The tibial bearing of claim 10 wherein the predominately surface sterilizing technology comprises a gas plasma spray process.

12. The tibial bearing of claim 10 wherein said polymeric material extends normally from the surface of said reinforcing component a distance of at least 5 millimeters.

13. The tibial bearing of claim 10 wherein said polymeric material comprises crosslinked ultra high molecular weight polyethylene.

14. The tibial bearing of claim 10 wherein said first centerline and said second centerline being non-coincidental.

15. The tibial bearing of claim 14 wherein the second centerline is parallel and spaced from the first centerline.

16. The tibial bearing of claim 10 wherein the reinforcing rod includes four spaced holes, two of the holes being in the first portion and two of the holes being in the second portion.

17. The tibial bearing of claim 16 wherein the two holes in the first portion are oriented substantially perpendicular to the first centerline and substantially perpendicular to each other and the two holes in the second portion are oriented substantially perpendicular to the second centerline and substantially perpendicular to each other.

18. The tibial bearing of claim 10 wherein the holes in the reinforcing rod are filled with polymeric material.

* * * * *

UNITED STATES PATENT AND TRADEMARK OFFICE
CERTIFICATE OF CORRECTION

| | | |
|---|---|---|
| PATENT NO. | : 8,083,802 B2 | Page 1 of 1 |
| APPLICATION NO. | : 12/050353 | |
| DATED | : December 27, 2011 | |
| INVENTOR(S) | : Gundlapalli et al. | |

It is certified that error appears in the above-identified patent and that said Letters Patent is hereby corrected as shown below:

<u>On the title page item [73]</u> the Assignee, should be changed from Deput Products, Inc. to read DePuy Products, Inc.

Signed and Sealed this
Twenty-eighth Day of August, 2012

David J. Kappos
*Director of the United States Patent and Trademark Office*